United States Patent [19]

Mueller-Lantzsch et al.

[11] Patent Number: 5,858,723
[45] Date of Patent: Jan. 12, 1999

[54] POLYPEPTIDES AND ANTIBODIES FOR DIAGNOSING AND TREATING SEMINOMA

[75] Inventors: Nikolaus Mueller-Lantzsch; Marlies Sauter, both of Homburg/Saar, Germany

[73] Assignee: Behringwerke Aktiengesellschaft, Germany

[21] Appl. No.: 567,336

[22] Filed: Dec. 5, 1995

[51] Int. Cl.$^6$ .............................. C12P 21/06; C12P 21/08
[52] U.S. Cl. ........................................ 435/69.3; 530/387.3
[58] Field of Search .......................................... 530/387.3

[56] References Cited

U.S. PATENT DOCUMENTS 5,134,227  7/1992  Chang et al. ............................. 536/27
5,175,098  12/1992  Watanabe et al. ..................... 435/69.3

FOREIGN PATENT DOCUMENTS

94/11514  5/1994  WIPO .

OTHER PUBLICATIONS

M. Sauter et al., "Human Endogeneous Retrovirus K10: Expression of Gag Protein and Detection of Antibodies in Patients with Seminomas", J. Virol. 69(1):414–421 (1995).
R. Loewer et al., "Identification of a Rev–Related Protein by Analysis of Spliced Transcripts of the Human Endogenous Retroviruses HTDV/HERV–K", J. Virol. 69(1): 141–149 (1995).
B. Hasenmaier et al., "The Activity of LTRs of the Endogenous Retrovirus HERV–K in Different Cell Lines", J. Cancer Res. Clin.Oncol. 119 suppl 1:54 abstract (1993).
W. Vogetseder et al., "Antibodies in Human Sera Recognizing a Recombinant Outer Membrane Protein Encoded by the Envelop Gene . . .", AIDS Res. Hum. Retroviruses 9(7): 687–694 (1993).
W. Vogetseder et al., "Human Endogenous Retrovirus K Does Not Encode Mouse Mammary Tumor Virus–Related Antigens in Human Breast Carcinomas", AIDS Res. Hum. Retroviruses 11(7):869–872 (1995).
N. Mueller–Lantzsch et al., "Human Endogenous Retroviral Element K10 (HERV–K10) Encodes a Full–Length Gag Homologous 73–kDa Protein and a Functional Protease", AIDS Res. Hum. Retroviruses 9(4): 343–350 (1993).
M. Ono et al., "Mucleotide Sequence of Human Endogenous Retrovirus Genome Related to the Mouse Mammary Tumor Virus Genome", J. Virol. 60(2): 589–598 (1986).
P. Stosiek et al., "Immunohistological Detection of Lymph Node Metastases in the Testicular Center as Quick Section Diagnosis During Retroperitoneal Lymphadenectomy", Path. Res. Pract. 189: 1010–1014 (1993).
K. Boller et al., "Evidence that HERV–K is the Endogenous Retrovirus Sequence that Codes for the Human Teratocarcinoma–Derived Retrovirus HTDV", Virol. 196: 349–353 (1993).
D. Bailey et al., "Production of a monoclonal antibody specific for seminomas and dysgerminomas", Proc. Natl. Acad. Sci. USA 83: 5291–5295 (1986).
N. Bartlett et al., "Serum Markers in Germ Cell Neoplasms", Hemat./Oncol. Clinics N.A. 5(6): 1245–1260 (1991).
A. Marks et al., "A novel anti–seminoma monoclonal antibody (M2A) labelled with technetium–99m: potential application for radioimmunoscintigraphy", Brit. J. Urol. 75: 225–229 (1995).

(List continued on next page.)

*Primary Examiner*—Jeffrey Stucker
*Assistant Examiner*—Hankyel Z. Park
*Attorney, Agent, or Firm*—Foley & Lardner

[57] ABSTRACT

Polypeptides are disclosed that are useful for diagnosing seminoma. The polypeptides have a sequence that corresponds to the amino acid sequence of the human endogenous retrovirus K10 (HERV-K10). Also disclosed are recombinant human endogenous retrovirus K10 (HERV-K10) env and gag polypeptides that are synthesized using genetic engineering techniques, constructs and processes for producing the recombinant polypeptides, and an assay for detecting the presence of antibodies specific for HERV-K10 env and/or gag polypeptides in human bodily fluids.

17 Claims, 10 Drawing Sheets

OTHER PUBLICATIONS

R. Mariani–Costantini et al., "Ancestry of a Human Endogenous Retrovirus Family", J. Virol. 63(11): 4982–4985 (1989).

A. Shih et al., "Evolutionary Implications of Primate Endogenous Retroviruses", Virol. 182: 495–502 (1991).

E. Larsson et al., "Human Endogenous Proviruses", Current Topics in Microbiol. Immunol. 148: 115–132 (1989).

S. Steinhuber et al., "Disbribution of human endogenous retrovirus HERV–K genomes in humans and different primates", Hum. Genet. 96: 188–192 (1995).

R. Loewer et al., "Identification of human endogenous retroviruses with complex mRNA expression and particle formation", Proc. Natl. Acad. Sci. USA 90: 4480–4484 (1993).

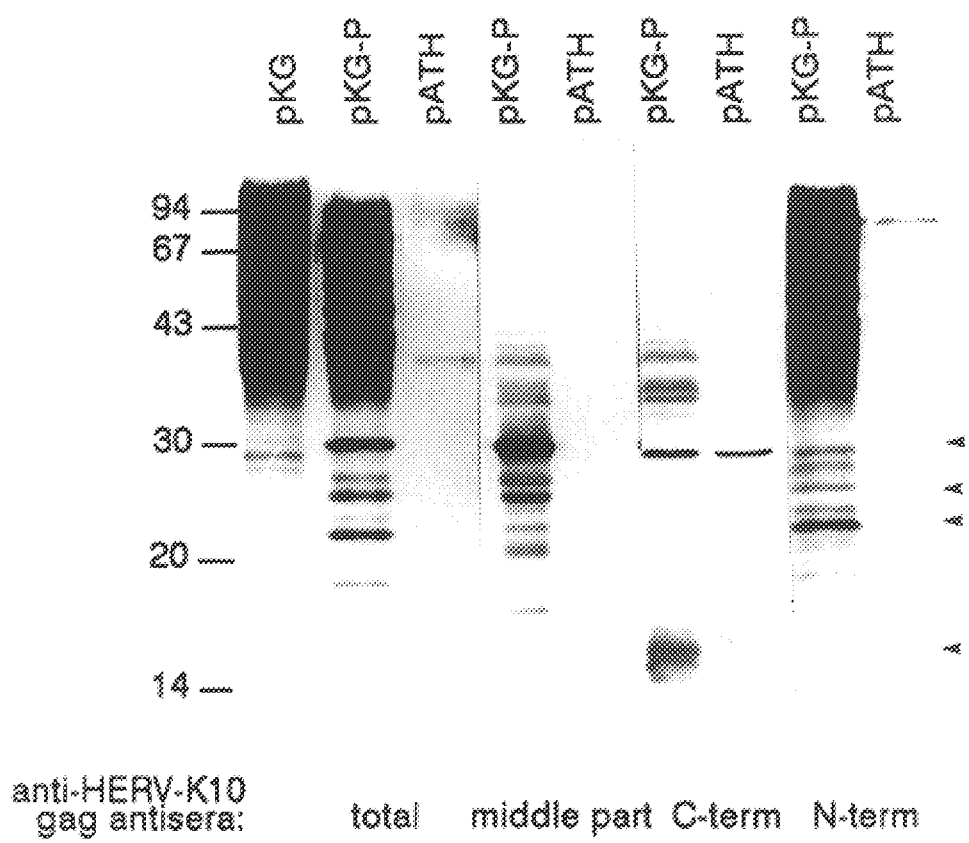

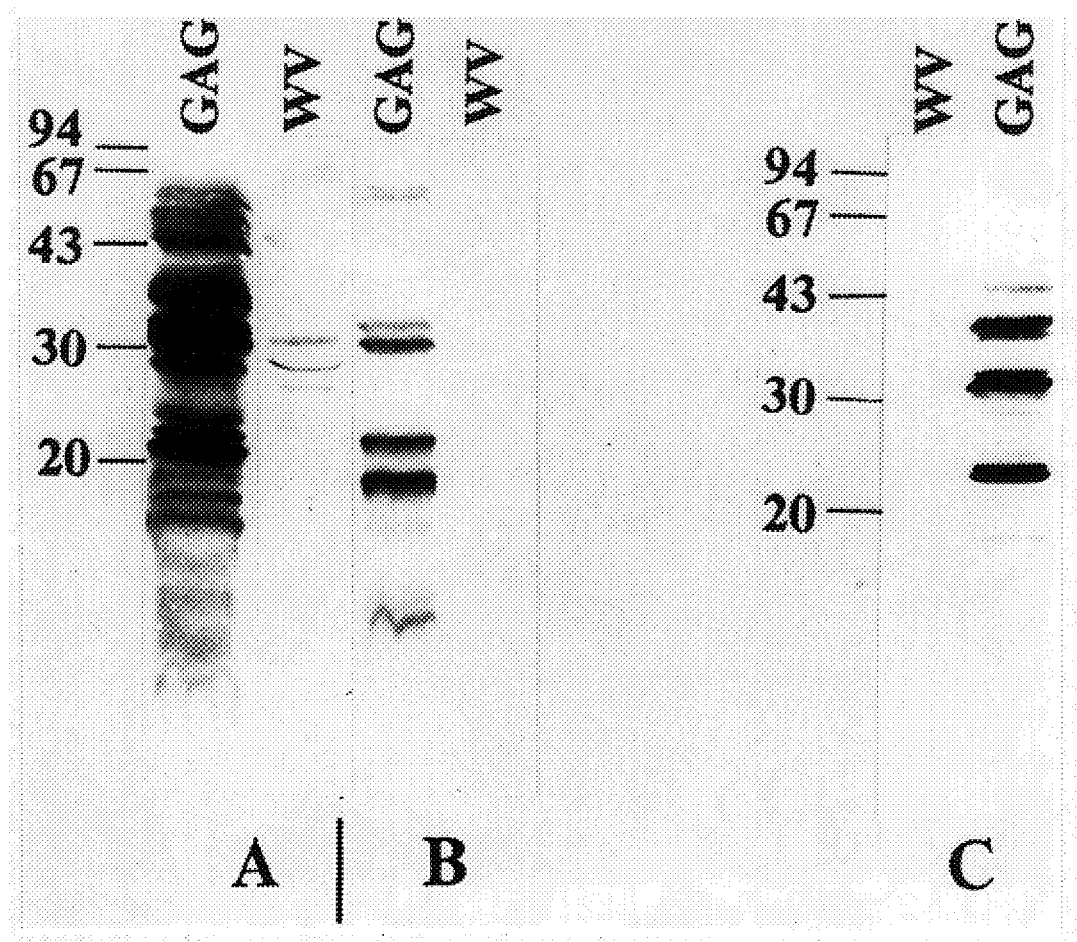

+: tunicamycin treatment

POLYPEPTIDES AND ANTIBODIES FOR DIAGNOSING AND TREATING SEMINOMA

FIELD OF THE INVENTION

The present invention relates to compositions and methods that are useful for diagnosing and treating diseases associated with the expression of polypeptides from the human endogenous retrovirus K10 (HERV-K10).

The compositions and methods of the invention are particularly useful for detecting and treating the presence of seminoma.

BACKGROUND OF THE INVENTION

Testicular cancer is the most common malignancy in men between 15 and 35 years of age. Seminoma is a type of germinal-cell tumor of the testes and accounts for half of the primary testicular tumors. Metastases are present in 10% of patients at initial presentation. Standard treatment for stage I seminoma, in which the tumor is confined to the testis and a lymphangiogram is negative, involves orchidectomy followed by ipsilateral irradiation of the para-aortic and pelvic lymph nodes. The treatment for Stage II seminoma, in which the tumor has spread to lymph nodes below the diaphragm, involves radiation treatment that extends to the involved anatomy.

About 10–20% of seminoma patients harbor micrometastases in the draining lymph nodes. Marks et al., *J. Urol.* 143:524 (1990). Therefore, the irradiation of regional lymph nodes as part of the standard treatment of Stage I seminoma is unnecessary in approximately 85% of all seminoma patients. Although post-orchidectomy radiation is generally well tolerated, local complications have been reported to include a higher incidence of second-site malignancies, impaired fertility, and persistent scrotal edema. Hunter, et al., *Cancer* 64:1608 (1989); Thomas, et al., *J. Urol.* 12:313 (1989).

These complications have led to the evaluation of post-orchidectomy surveillance without radiation as an alternative to management of stage I seminoma. Thomas, et al., supra (1989); Germalluch et al., *Br. J. Urol.* 73:172 (1994); Peckham et al., *Br. J. Urol.* 59:343 (1987). The instant invention is a response to the need for improved assays to detect the most common malignancy in adolescent and young adult men before it metastasizes and for detecting any recurrence of seminoma in seminoma patients.

In this context, therefore, a need exists for a highly sensitive and specific system for detecting the presence of seminoma that is safe and easy to manufacture and perform. Such a method would permit approximately 85% of all seminoma patients to avoid the complications associated with lymph node irradiation. In addition, a method that detects the presence of a seminoma may also be used to screen for residual seminoma or a relapse of the tumor.

SUMMARY OF THE INVENTION

It is therefore an object of the present invention to provide a highly sensitive and specific assay for seminoma.

It is a further object of the present invention to provide an assay for diagnosing seminoma that is safe, inexpensive to manufacture and easy to use.

It is yet another object of the present invention to provide a method to detect the presence of HERV-K10 gag and/or env proteins expressed in seminoma tumor cells.

It is a further object of the present invention to detect and titer the presence of antibodies against HERV-K10 gag and/or env in samples from patients with seminoma.

It is a further object of the present invention to provide a method to detect the presence of HERV-K10 gag and/or env proteins to diagnose the presence of a particular disease state that correlates with the expression of env and/or gag polypeptides from the human endogenous retrovirus K10 (HERV-K10) It is another object of the present invention to provide methods for detecting HERV-K10-specific antibodies.

It is a further object of the present invention to provide methods for producing antigens for detecting HERV-K10 specific-antibodies.

In accomplishing the foregoing objects, there has been provided in accordance with one aspect of the present invention, a method for determining HERV-K10 specific antibodies in a patient comprising the steps of (1) providing a recombinant HERV-K10 antigen capable of binding to anti-HERV-K10 specific immunoglobulin in a sample obtained from the patient, wherein the HERV-K10 antigen is produced by expressing a recombinant DNA encoding the antigen; (2) immobilizing the antigen directly or indirectly on a surface; (3) incubating the immobilized antigen with a solution comprising a sample to be determined under conditions effective for binding anti-HERV-K10 immunoglobulins in the sample to the immobilized HERV-K10 antigen and, (4) determining the immunoglobulin bound to the immobilized HERV-K10 antigen.

Other aspects of the invention provide compositions that are useful in the foregoing method. Such compositions include HERV-K10-specific antibodies and polypeptides. For example, HERV-K10-specific polypeptides include a eukaryotically expressed HERV-K10 gag and/or env polypeptide, fusion protein or a derivative of thereof. Other HERV-K10 specific proteins include the N-terminus of the HERV-K10 gag protein or derivatives. Also, HERV-K10 env protein containing the transmembrane region, either with or without the signal peptide and amino terminus are particularly preferred, as most antibodies to the envelope protein are directed against the transmembrane-region of the envelope protein.

Another aspect of the invention includes the expression of the HERV-K10 antigen via a recombinant DNA encoding the antigen, wherein the recombinant DNA comprises a baculovirus polyhedrin promoter operably linked to a cDNA encoding the antigen and expression of the antigen by the promoter is in *Spodoptera frugiperda* cells. Particularly preferred in this aspect of the invention, is the plasmid pKG-P.

Other aspects of the invention include therapeutic methods, such as HERV-K10-specific antibodies conjugated to antitumor agents and HERV-K10-specific polypeptides useful as vaccines to prime the immune system against tumors, such as seminoma, that express HERV-K10 polypeptides. Yet another aspect of the invention includes diagnostic methods for detecting pathological tissues expressing HERV-K10 env and gag polypeptides, such as seminoma. Such diagnostic assays include: (1) the use of HERV-K10 env or gag polypeptides to detect antibody titers in diseased patients, (2) immunofluorescence or immunohistochemistry to detect HERV-K10 gag and/or env polypeptides in seminoma and (2) immunoscintography to detect the presence of HERV-K10 gag and/or env expressing tissues, such as seminoma, in vivo.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 2A. Procaryotic expression and immunoblot analysis of HERV-K10 gag protein products by the constructs pKG containing the gag-homologous region of HERV-K10, pKG-P containing the protease gene in addition to the gag-homologous region, or the vector pATH alone as described below under the "Characterization of the HERV-K10 Gag proteins." Five $\mu$gs. of total bacterial protein is subjected to a 15% SDS-PAGE. After blotting the filter-membranes are probed with an anti-Gag polyclonal rabbit serum, a polyclonal rabbit serum raised against the N-terminal part (pKN0.7) of the Gag protein and monoclonal antibodies generated against the middle part (pAUR-1) or against the C-terminal part (pKP0.8) of the Gag protein. The apparent molecular masses are calculated from co-migrating molecular weight standards and are given in kilodaltons (KDa).

FIGS. 4A, 4*b* and 4C. Eukaryotic expression of HERV-K10 gag expressed in the baculovirus system. The insect cells *Spodoptera frugiperda* were infected either with the wild type baculovirus *Autographa californa* (WV) or with a recombinant baculovuris containing the HERVK-10 gag-homologous regions (GAG) (See FIG. 1). The cells were harvested 24 hours after infection, suspended in sample buffer and 5 ug of the protein was subjected to a 15% SDS PAGE following blotting analysis with an anti-gag polyclonal rabbit serum (FIG. 4A), monoclonal antibodies against the middle part of the gag-protein (FIG. 4B), and monoclonal antibodies directed against the C-terminal part of the gag-protein (FIG. 4C). The apparent molecular masses were calculated from comigrating molecular weight standards and are given in kilodaltons.

FIG. 7A. Insect cells are treated (+) or untreated(−) with tunicamycin (2.5 $\mu$g/ml). The immunoblotting analysis is performed with the polyclonal anti-OM serum as described in FIG. 6.

FIG. 7B. The immunoblotting analysis is performed with an anti-HERV-K10 env positive human serum from a patient with a seminoma. The apparent molecular masses are calculated from co-migrating moLecular weight standards and are given in kilodaltons.

DETAILED DESCRIPTION OF PREFERRED EMBODIMENTS

Figure 1A:
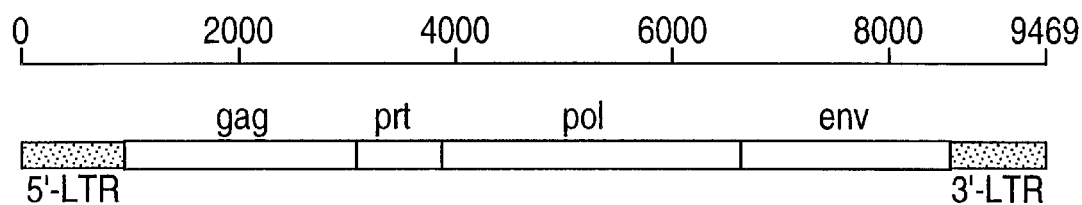
FIG. 1A is a schematic diagram of the HERV-K10 gene and the segments of the gene that encode polypeptides according to the present invention.

A premise for the instant invention has resulted from the recognition that HERV-K10 gag and/or env proteins are synthesized in seminoma cells and that patients with those tumors exhibit relatively high antibody titers against HERV-K10 gag and/or env. Prior to the present invention, the use of HERV-K10 proteins and HERV-K10-specific antibodies in the detection of seminoma or the treatment of seminoma had not been realized.

Human endogenous retroviruses (HERVs) or human endogenous proviral DNAs have been identified in human genomic DNA by their homology to retroviruses of other vertebrates. See Larsson, E., et al., *Current Topics in Microbiology and Immunology* 148:115 (1989); Mariani-Costantini, et al., *J. Virol.* 63:4982 (1989) and Shih, et al., *Virology* 182:495 (1991). Although it is believed that the human genome probably contains numerous copies of proviral DNAs, nothing is known about their function.

Proviral DNAs are divided into distinct families based on different degrees of homology and other features. Recently, it was shown that the proviral element-K10 contains an open pol reading frame as well as open gag and env reading frames while all other proviral elements exhibit reading frames with multiple stop codons. Ono, et al., *J. Virol.* 60:589 (1986); Loewer, et al., *Proc. Natl. Acad. Sci USA* 90:4480 (1993); Mueller-Lantzsch, and Sauter, et al., *AIDS Research and Human Retroviruses* 9:343 (1993) and Larsson, supra. Semiquantitative Southern blot analysis of genome copy numbers revealed that the HERV-K10 element is present in 25 to 30 copies or more within the genome of human individuals. Mueller-Lantzsch and Sauter, et al., supra (1993) and Ono, et al., supra (1986). Prokaryotic expression of HERV-K10 gag and prt region demonstrated that this element encodes a full-length gag homologous 73-KDa protein and a functional protease which is located in a −1 position to the reading frame of gag. Ono et al., supra. Expression of proviral DNA, especially of HERV-K, has been observed in placental tissue, teratocarcinoma cell lines, and breast cancer cell lines by detection of distinctly sized transcripts. Franklin, et al., *J. Virol.* 62:1203 (1988); Kato, et al., *J. Virol.* 61:2182 (1987); Loewer, et al., supra (1993) and Ono, et al., *J. Virol.* 61:2059 (1987). The expression of HERV-K10 gag polyprotein and processed protein in a teratocarcinoma-derived cell line (GH) has been described. Boller, et al., *Virol.* 196:349 (1993). Also, particles related to HERV-K are released from GH cell in the supernatant. Id. However, prior to the instant invention, nothing was known about the function of HERV-K genes or a possible association between HERVs and human diseases. It had only been speculated that HERV might play a role in autoimmunity. Query, et al., *Cell* 51:211 (1987).

One aspect of the instant invention is the recognition that HERV-K10 gag and/or env proteins are synthesized in seminoma cells and that patients with those tumors exhibit relatively high antibody titers against gag and/or env.

HERV-K10(+) contains a 290 base pair insert at the pol env junction. Ono et al., supra. The sequences published by Ono of HERV-K10 represents two types of proviral genome that differ in the env gene region. A stop codon interrupts the env homologous region into two open reading frames. HERV-K10(+) exhibits the sequences for a putative signal peptide (SP), an outer membrane protein (OM), and the transmembrane protein (TM). The env region of HERV-K10, as compared to HERV-K10(+), lacks the sequences for the SP and a small N terminal part of the env gene. Sequence analysis of pACENV1.9(+) revealed significant differences to the published sequence. Twenty-one nucleotide exchanges and an insertion after nucleotide 6686, based on the numbering for the HERV-K10(+) by Ono et al., supra, result in remarkable alterations in the 5' region of the env gene and in additions to a combined env reading frame capable of encoding a functional env protein. The instant analysis of the sequence of the HERV-K10 env gene is in agreement with the findings of Loewer et al., *Proc. Natl. Acad. Sci. USA* 90:4480 (1993) and Loewer et al. *J. Virol.* 69:141 (1995).

Another aspect of the invention provides eukaryotic cells that express recombinant HERV-K10 gag and env proteins, to the HERV-K10 gag and env proteins themselves, and to processed portions or fragments thereof, which are capable of detecting the presence of antibody titers to HERV-K10 gag and/or env when primary or recurring seminoma is present. The present invention also relates to HERV-K10 gag and env proteins and to processed portions or fragments thereof, which are capable of detecting the presence of antibody titers to HERV-K10 env and gag, respectively, when primary or recurring seminoma is present.

Many available immunoassays or enzyme immunoassays (EIAs) to detect antibodies to viral proteins rely on whole virus from cell culture. It is believed that HERV-K10-like particles are biologically defective, as all attempts to cultivate HERV-K10 have been unsuccessful. Thus, there is a need for a safe and convenient method to produce large quantities of HERV-K10 antigens suitable for diagnostic applications.

The production of HERV-K10 recombinant proteins in heterologous host cells via the expression of cloned genes would provide a virtually unlimited source of HERV-K10 antigens suitable for use in immunoassays to detect the presence of HERV-K10. Moreover, expressing proteins by recombinant means allows for low batch to batch variation and greater ease in calibrating and quantitating assays.

Gag polypeptide molecules can be produced based on the long open reading frame "ORF1/2" encoding the HERV-K10 gag protein disclosed by Mueller-Lantzsch et al., *AIDS Research and Human Retroviruses* 9:342 (1993) or the HERV-K10 env sequences in the two open reading frames ORF1 and ORF2 disclosed by Ono, et al., *J. Virol.* 60:589 (1986). Env polypeptide molecules can be produced based on open reading frames 5 and 6 encoding the HERV-K10 env protein disclosed by Mueller-Lantzsch et al., supra (1993) and the HERV-K10 env sequences disclosed by Ono, et al., *J. Virol.* 60:589 (1986). The polypeptides of the instant invention can be produced by recombinant DNA technology employing the nucleotide and corresponding amino acid sequences disclosed in Table 2 of Mueller-Lantzsch et al., *AIDS Research and Human Retroviruses* 9:342 (1993) or in Ono, et al., supra. Mueller-Lantzsch, et al., supra (1993) discloses 41 nucleotide changes that result in 20 amino acid exchanges in comparison to the published HERV-K10 sequence of Ono et al., supra. Tables I-A through I-C document these differences.

Polypeptide molecules also can be produced that (1) include sequence variations, relative to the naturally-occurring sequences, (2) have one or more amino acids truncated from the naturally-occurring sequences and variations thereof, or (3) contain the naturally-occurring sequences and variations thereof as part of a longer sequence. In this description, polypeptide molecules in categories (1), (2) and (3) are said to "correspond" to the amino acid sequences of the HERV-K10 gag or the HERV-K10 env protein. Such polypeptides also are referred to as "variants." The category of variants within the present invention includes, for example, fragments and muteins of the C-terminal or the N-terminal (pKN0.7) part of the HERV-K10 Gag protein, such as those produced by pKP0.8 or pKN0.7, respectively, as well as larger molecules that consist essentially of one or both of the HERV-K10 gag and env sequences, alone or in combination with other proteins, such as fusion proteins. It is noted that variants do not include related env and gag polypeptides or gene products that are not HERV-K10, such as the mouse mammary tumor virus (MMTV) env product (Majors, et al., *J. Virol.* 47:495 (1983); Redmond, et al., *EMBO J.* 2:125 (1983)).

In this regard, another aspect of the invention provides an HERV-K10 env polypeptide or HERV-K10 gag polypeptide, alone or in combination, which reacts immunologically with a sample from a person with primary seminoma, seminoma relapse, primary mixed tumor with seminoma, mixed tumor with seminoma-relapse, or teratoma-teratocarcinoma-mixed tumors with teratoma-yolk sac-chorioembryocarcinoma. However, the preferred molecules of the invention do not react immunologically with a sample from a healthy person or patients with seminoma in remission, other testicular abnormalities, mixed tumor with seminoma in remission, teratoma/teratocarcinoma-mixed tumors with teratoma-yolk sac-chorioembryocarcinoma in remission, testicular abnormalities, or autoimmune disorders.

A "mutein" is a polypeptide that is homologous to the HERV-K10 gag or env proteins to which it corresponds, and that retains the basic functional attribute, namely the ability to react selectively with samples from persons with seminoma. For purposes of this description, "homology" between two sequences connotes a likeness short of identity indicative of a derivation of the first sequence from the second. In particular, a polypeptide is "homologous" to the corresponding HERV-K10 gag or env polypeptide if a comparison of amino-acid sequences between the recombinantly produced polypeptide and the corresponding viral protein reveals an identity of greater than 70%. Such a sequence comparison can be performed via known algorithms, such as the one described by Lipman and Pearson, which are readily implemented by computer. Polypeptides derived from HERV-K10 that are homologous to the sequences disclosed by Mueller-Lantzsch et al., supra (1993) and Ono, et al., supra (1986) constitute naturally-occurring muteins and are within the scope of the present invention. As discussed above with regard to the HERV-K10 polypeptide variants of the instant invention, HERV-K10 muteins also do not include related env and gag polypeptides or gene products that are not HERV-K10.

HERV-K10 encodes a 73,000 KDa gag protein which is processed by an HERV-K10-encoded protease to yield proteins p22/p26, p30 and p15/16. The instant invention expresses the gag and/or env gene of HERV-K10 in bacterial or eukaryotic cells. Preferred bacterial cells are E. coli, while the preferred eukaryotic cells are insect cells. These recombinant products are used to test antisera from patients with different diseases and healthy individuals and are able to detect antibodies against the HERV-K10 gag and/or env polypeptides.

A fragment of an HERV-K10 gag or env polypeptide is a molecule in which one or more amino acids are truncated from these proteins. Muteins and fragments can be produced, in accordance with the present invention, by known de novo synthesis techniques.

Also exemplary of variants within the present invention are molecules that are longer than the known HERV-K10 gag or env polypeptides but that contain the region or a mutein thereof within the longer sequence. For example, a variant may include a fusion partner in addition to the amino-terminus of the HERV-K10 gag protein. Such a fusion partner may allow easier purification of recombinantly-produced polypeptides. For example, use of an anthranilate synthetase protein (TrpE), β-galactosidase (β-gal) or glutathione-S-transferase (26 kilodaltons, GST) as a fusion partner allows purification of recombinant polypeptides.

It will be appreciated that polypeptides shorter than the corresponding gag or env polypeptides but that retain the ability to react selectively with samples from persons with seminoma or conditions expressing HERV-K10 gag or env are suitable for use in the present invention. Thus, variants may be of the same length, longer than or shorter than the gag or env polypeptides, and also include sequences in which there are amino acid substitutions of the parent sequence. These variants must retain the ability to react selectively with samples from persons seminoma or expressed HERV-K10 env or gag protein.

Whether a polypeptide of the instant invention retains the ability to react selectively with samples from persons with seminoma or expressed HERV-K10 env or gag can be determined routinely in accordance with the protocols set forth herein, that is, by reacting it with serologically well-characterized specimens from patients known to have seminoma.

Figure 1B:
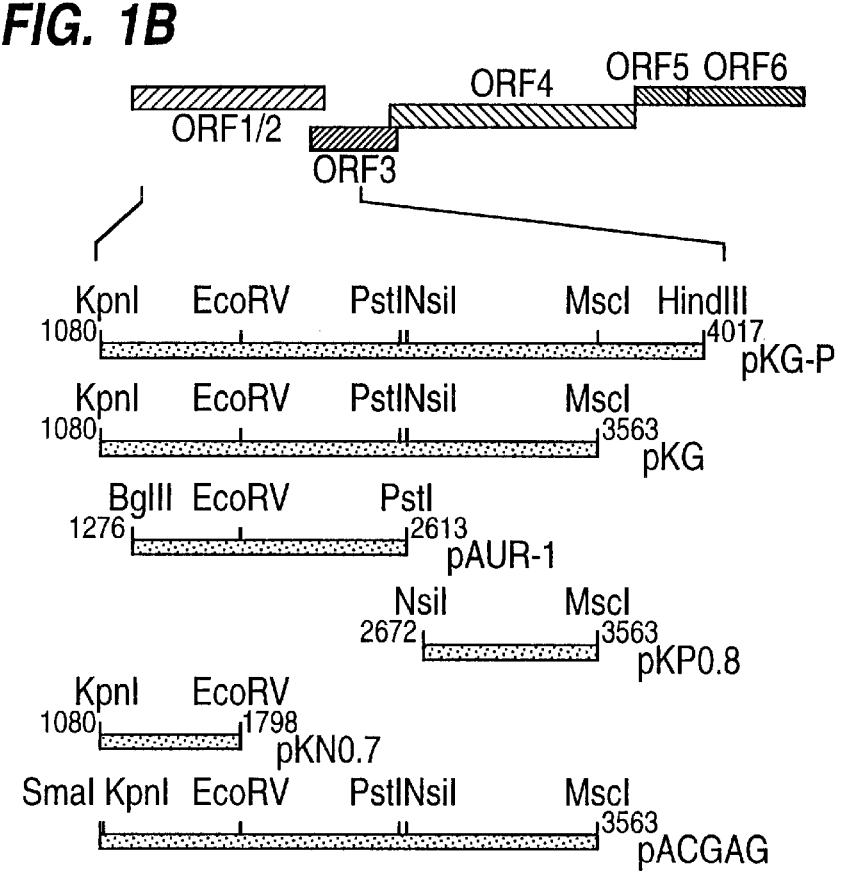
FIG. 1B is a schematic representation of the plasmids which are used for procaryotic expression of HERV-K10 gag (pKG-P, pKG), for eukaryotic expression of HERV-K10 gag (pACGAG), for expressing protein to raise polyclonal rabbit sera against HERV-K10 gag (pKG, pAUR-1, pKN0.7, pKP0.8), and for expressing protein to generate monoclonal antibodies against HERV-K10 gag (pAUR-1, pKP0.8).

A schematic diagram of the restriction map and open reading frames (ORFs) of the HERV-K10 genome is shown in FIG. 1A. The horizontal rectangle labelled ORF 1/2 depicts the portion of the genome encoding HERV-K10 gag. The sequence analysis reported by Mueller-Lantzsch, et al., supra (1993) revealed an insertion of a guanidine nucleotide between positions 1749 and 1750 in the sequence published by Ono, et al., supra (1986), which results in a frame shift combining ORF1 and ORF2 and generating a long open reading frame of at least 1337 base pairs within the gag region of HERV-K10. Tables I-A, I-B and I-C summarize the nucleotide and resulting amino acid sequences exchanges described by Mueller-Lantzsch, et al., supra (1993) as compared to the HERV-K10 sequences described by Ono, et al., supra (1986). The horizontal rectangles labelled ORF5 and ORF6, together depict the portion of the HERV-K10 genome encoding HERV-K10 env. Restriction sites are indicated by KpnI, EcoRv, PstI, NsiI, MscI, HindIII. Schematic representations of the plasmids that are used for procaryotic expression of HERV-K10 gag polypeptide (pKG-P, pKG), for eukaryotic expression of HERV-K10 gag polypeptide (pACGAG), for raising polyclonal rabbit sera to HERV-K10 gag (pKG, pAUR-1, pKN0.7, pKP0.8), and for generating monoclonal antibodies to HERV-K10 gag (pAUR-1, pKP0.8) are shown in FIG. 1B.

Recombinant polynucleotides for the production of a fusion protein recombinant polypeptide that includes the HERV-K10 gag and/or env polypeptides may be constructed. For example, one method to produce HERV-K10 gag-specific polypeptides is to insert the entire gag region of HERV-K10 into an expression vector for expression in E. coli to specifically process HERV-K10 gag polyprotein by the HERV-K10-encoded protease. Sauter, et al., J. Vir. 69:414 (1995).

On method for producing GST fusion proteins, for example, involves inserting recombinant polynucleotides into plasmid pGEX. The gene encoding GST is positioned upstream from the SmaI site into which the TCR27 segments are inserted, and thus the recombinant polypeptides encoded by these plasmids have GST attached to their N-termini. The presence of GST allows purification of the recombinant polypeptides on glutathione agarose beads, but it will be readily apparent to those of ordinary skill in the art that the GST fusion partner can be cleaved from polypeptides to be used in an assay according to the invention.

Polypeptides useful in an assay according to the invention can be synthetic peptides made by chemical synthesis techniques based on the amino acid sequences disclosed in Mueller-Lantzsch, et al., supra (1993), but preferably are produced by recombinant techniques. Polypeptides of the instant invention are obtained preferably by recombination of DNA sequences encoding the HERV-K10 gag and/or env proteins disclosed by Mueller-Lantzsch, et al., supra (1993) or Ono, et al., supra (1986).

These DNA segments are utilized to produce recombinant polypeptides. Proteins expressed in prokaryotic and simple eukaryotic systems such as yeast, often display immunological characteristics different from their natural counterparts. Such differences can limit the utility of recombinant proteins in assays that require recognition of serum antibodies that bind to native protein. To circumvent such problems, recombinant baculoviruses are employed for the high-level expression of genes in higher eukaryotes. Success in constructing vectors that produce protein products has been achieved for other proteins, and studies of these proteins show that post-translational modifications are similar in insect and mammalian cells, although glycosylation varies in detail.

The use of eukaryotic expression systems to produce the proteins of the instant invention is also preferred because bacterial proteins exhibit higher cross-reactivity with human antisera than insect cell proteins. HERV-K10 gag or env expressed in bacterial systems should be purified from bacterial protein before they can be used in detecting HERV-K10 specific antibodies. In order to avoid the extra purification steps that bacterially expressed proteins require, the baculovirus expression system is a preferred method of producing HERV-K10 gag and env proteins for use in the instant invention.

The N-termini or the C-termini of these polypeptides can be modified, respectively, to include a linker sequence that facilitates attachment or conjugation of the portions of the polypeptides that constitute the reactive epitopes to carrier molecules in solution or to solid support systems.

These techniques are useful to alter patterns of post-translational modification For instance, changes in the amino acid sequence of a protein can alter its glycosylation or phosphorylation pattern. Such techniques are also useful to provide specific functional moieties that aid efficient expression or purification of recombinantly expressed proteins, inter alia. In accordance with the invention, it will be understood, therefore, that the entire panoply of recombinant DNA techniques can be employed to provide antigens useful to detecting anti-HERV-K10 immunoglobulins.

A variety of expression systems may be used to produce HERV-K10 polypeptide or antigens in accordance with the invention. For instance, a variety of expression vectors suitable to producing proteins in *E. coli, B. subtilis*, yeast, insect and mammalian cells have been described, any of which might be used in accordance with the invention to produce an HERV-K10 antigen suitable to detect anti-HERV-K10 antibodies in exposed patients. Whereas expression in more rudimentary systems such as bacteria and yeast often results in high levels of protein, post-translational modifications important to antigenicity often are not made in such systems. In contrast, mammalian systems that properly process a protein as it is produced from a mammalian cell often result in low yields. Among the expression systems useful for producing the HERV-K10 gag and env polypeptides of the invention, the baculovirus expression system can be used to express large quantities of a foreign protein and provide the necessary processing; baculovirus is therefore highly preferred. Particularly preferred in this regard is the baculovirus expression system that utilizes the polyhedrin promoter to direct expression of HERV-K10 antigens. Matsura et al. (1987) *J. Gen. Virol.* 68:1233–1250.

Figure 7A:
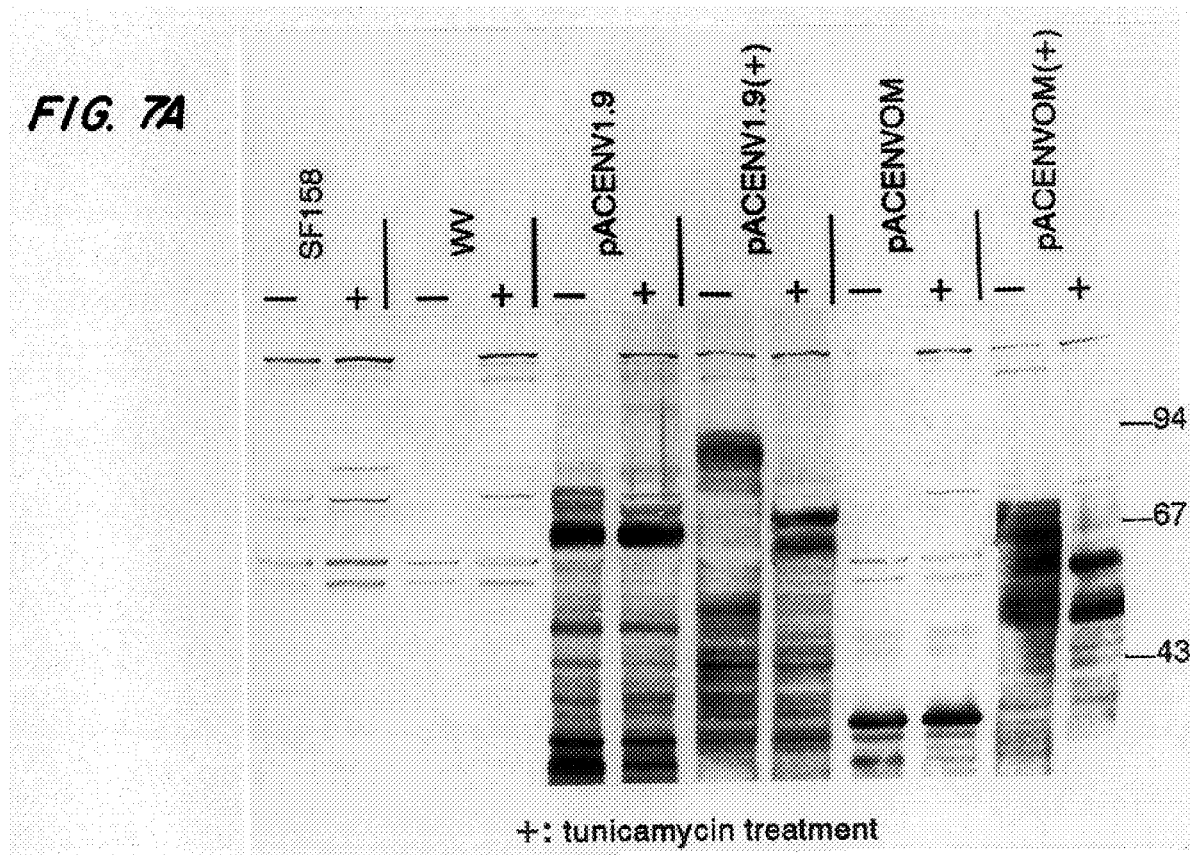
FIGS. 7A and 7B. Protein analysis of insect cells (SF158) infected with wild type baculovirus (WV) or with recombinant baculovirus containing different parts of the env homologous region described in FIG. 1C.
Figure 7B:
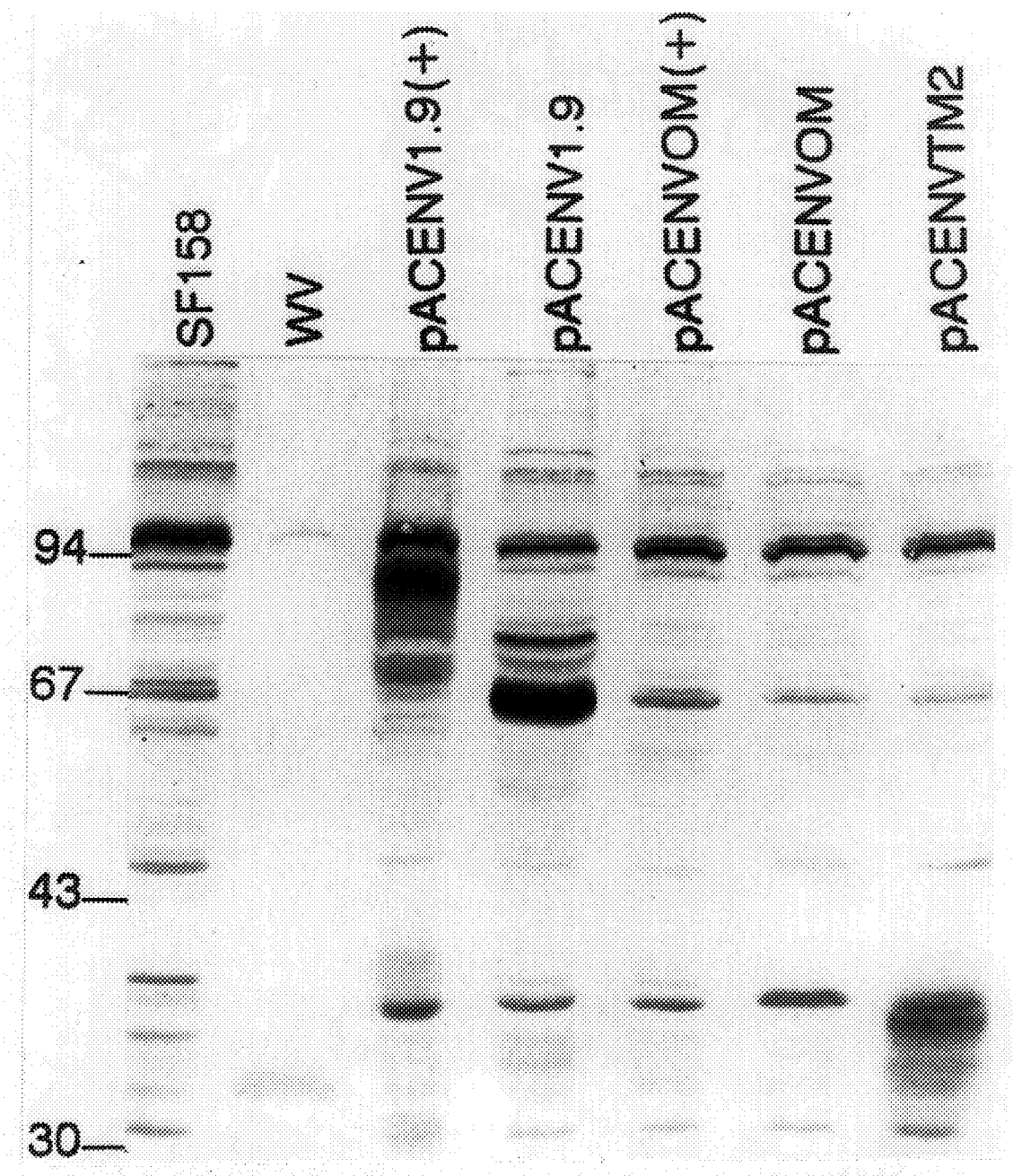

The tunicamycin data, presented in FIG. 7, indicates that glycosylation is not required for the TM region of HERV-K10 env to react with human antibodies. For this reason, the baculovirus system is not required to produce an immunologically-positive HERV-K10 env. Nonetheless, the baculovirus expression system is preferred because it provide; recombinant HERV-K10 proteins that are less contaminated than bacterially expressed proteins, as the latter includes bacterial proteins that exhibit higher cross-reactivity with human antibodies than insect cell produced proteins.

Antigens produced in accordance with the invention can be used in a variety of immunological assays to detect anti-HERV-K10 antibodies in a patient. In fact, it will be readily appreciated by those of ordinary skill that antigens according to the invention can be used in practically any immunological assay for detection of HERV-K10-specific antibodies.

The present inventive method further relates to methods for diagnosing diseases associated with the expression of HERV-K10 gag and/or env proteins, such as seminoma, by detecting antibodies that bind specifically to the polypeptides. The method consists of bringing into contact a sample of whole blood, or an antibody-containing bodily sample, with a polypeptide, according to the invention. The polypeptide may be attached or conjugated to a carrier molecule or solid phase. After a period of contact between the sample and the polypeptide, during which antibodies in the sample are bound to the polypeptide, unbound antibodies are washed away. The bound antibodies are then visualized or otherwise detected by adding a compound or compounds that detect the antibodies which are specifically bound to the polypeptides. Exemplary of compounds that enable detection of the anti-HERV-K10 antibodies are colorometric agents, fluorescent agents, chemilluminescent agents and radionuclides.

The assays include direct and indirect assays, sandwich assays, solid phase assays such as those using plates or beads among others, and liquid phase assays, inter alia. Assays suitable for use in the invention include those that use primary and secondary antibodies, and those that use antibody binding reagents such as protein A. Moreover, a variety of detection methods can be used in the invention, including calorimetric, fluorescent, phosphorescent, chemiluminescent, luminescent and radioactive methods.

A significant feature of the present invention is that it enables the use of HERV-K10 gag and/or env proteins to which seminoma patients produce antibodies, in a method of diagnosing seminoma. In accordance with the present invention, preparations formulated from polypeptides which are produced recombinantly or by chemical synthesis, respectively, are "substantially pure." That is, they do not contain other proteins or polypeptides of tumor or testicular origin. In addition, the detection of HERV-K10 env and/or gag is specific to seminoma in males, in contrast to other serum markers in germ cell neoplasms such as alpha-fetoprotein (AFP) or the beta subunit of human chorionic gonadotropin (BHCG). See Bartlet et al., *Germ Cell Neoplasms in Hematology/Oncology Clinics of North America* 5:1245 (1991).

A high percentage of blood specimens from seminoma patients have demonstrable specific antibodies to HERV-K10 gag and/or env polypeptides according to the invention. In contrast, specimens from healthy persons rarely contain such antibodies (0.7%; See Table II). Equally important, specimens from patients with diseases that could be associated with false-positive reactions, such as seminoma in remission or autoimmune diseases, did not produce false positives in assays with polypeptides according to the present invention. Thus, the present polypeptides are useful for diagnosing primary seminoma and recurrent seminoma.

The present invention can be understood further with reference the following, non-limiting examples.

EXAMPLE 1

Identification of HERV-K10 Env and/or Gag in Cancer-Derived Cell Lines

In order to determine if HERV-K10 env and/or gag are expressed in various cancer-derived cell lines, pellets (cell membranes and organelles) and supernatant (soluble fractions) from lysed cell lines are tested for the presence of expressed HERV-K10 products using a polyclonal antisera against HERV-K10 gag or env. The cell lines Tera 1, a teratocarcinoma cell, and T47D, a mammacarcinoma cell, are obtained from the American Type Culture Collection. Keydar, et al., *Eur. J. Cancer* 15:659 (1979); Fogh, et al., *In Human Tumor Cells in Vitro* (Fogh J, ed). New York: Plenum Press 115 (1975). The B95-8 cell line was originally established by infecting marmoset B lymphocytes with Epstein-Barr virus. Miller, et al., *Proc. Natl. Acad. Sci. USA* 70:190 (1973). Tera 1 cells are maintained in McCoy's 5a medium supplemented with 10% fetal calf serum, 40 U of penicillin/ml and 50 µg of streptomycin/ml and are subcultured once a week. Tera 1 and T47D cells are grown in plastic tissue culture flasks. Transfer of Tera 1 cells is performed by shaking off the loosely adhering cells from the culture flasks. For subculturing of T47D cells a standard trypsin treatment is used. B95-8 and T47D cells are maintained in RPMI-1640 medium supplemented with 10% fetal calf serum, 40 U of penicillin/ml, 50 µg of streptomycin/ml, 10 U of moronal/ml and 10 µg of neomycin sulfate/ml and are subcultured once or twice a week.

Figure 2B:
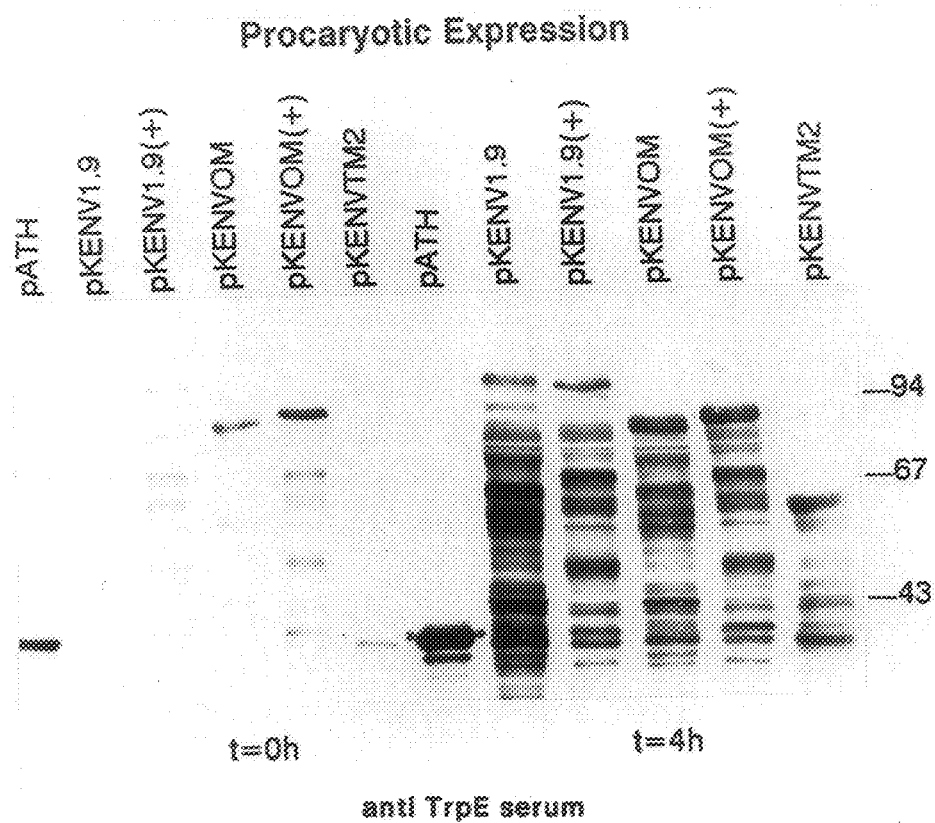
FIG. 2B. Procaryotic expression of HERV-K10 env proteins in the vector system pATH. *E. coli* Bl21-DE-3 cells are transformed with the constructs shown in FIG. 1C, cells are harvested at the time of induction and 4 hours after induction, suspended in sample buffer and 5 $\mu$g of total protein is subjected to 13.5% SDS-PAGE. After blotting the membranes are probed with an anti-TrpE monoclonal antiserum. The apparent molecular masses are calculated from co-migrating molecular weight standards and are given in kilodaltons.

B95-8 is an HERV-K10 negative New World monkey cell line. To yield the supernatant extracts (SN), the culture supernatant is removed from cells and debris by low speed centrifugation and are filtered through a 0.45 µm disposable filter. Subsequently, the supernatant is centrifuged for 3 hours at 100,000×g. The resulting pellets are resuspended in sample buffer and 1 µg is subject to a 15% SDS-PAGE. After blotting, the filtermembranes are probed either with rabbit sera directed against the middle part (pAUR-1), the C-terminal part (pKP0.8), the N-terminal part (pKN0.7) or the entire gag protein (total, pKG) as indicated in FIGS. 1B and 2A. Controls are performed on similarly prepared blots using preimmune serum.

In order to study the expression and the processing of the gag polyprotein in more detail, protein extracts from the teratocarcinoma cell line Tera 1 and the 100,000×g pellet of the supernatant of this cell line are analyzed by immunoblotting using different specific rabbit anti HERV-K10 Gag sera or monoclonal antibodies. The investigation of Tera 1 cell extracts using a serum against the entire Gag polyprotein (serum No. 6897) revealed the existence of a 80 KDa protein which seems to correspond to the full length Gag polyprotein. Further protein bands of approximately 70 KDa, 53 KDa and 39 KDa could be identified representing partially processed Gag proteins. Analyzing the 100,000×g pellet of the supernatant from Tera 1 cells by the same method additional protein bands of 30 KDa, 22 KDa, 19 KDa and 17 KDa could be observed. The corresponding material from HERV-K10 negative B95-8 cells (New world monkey) or T47D cells served as a control.

Figure 3A:
FIGS. 3A and 3B. Tentative location of the processed HERV-K10 gag proteins: procaryotic expressed gag protein in *E. coli* (FIG. 3A) and gag protein expressed in Tera 1 cells (FIG. 3B).
Figure 3B:
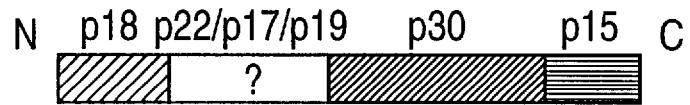

Analyzing the 100,000×g pellet by using rabbit antisera against different part of the Gag polyprotein it is possible to construct a tentative order of processed HERV-K10 Gag proteins expressed in the cell line Tera 1 (FIG. 3B). For example, a 15 KDa protein is recognized only by the serum against the C-terminus while a 30 KDa protein reacted most dominantly with the serum directed against the middle part of HERV-K10 Gag. In addition, a 18 KDa protein is identified by the serum against the N-terminus.

The 22, 19 and 17 KDa proteins are located on the HERV-K10 gag gene. These proteins are detected by the antiserum against the middle part of gag. Only the 22 KDa exhibit a weak reaction with the N-terminal directed serum. Concerning the C-terminal part of HERV-K10 gag the prokaryotic expression in *E.coli* and the expression of HERV-K10 gag in Tera 1 cells revealed good correspondence.

EXAMPLE 2

Expression of HERV-K10 Gag and Env Polypeptides

The instant invention recombinantly expresses HERV-K10 gag and env encoded proteins and identifies their association with seminoma. Using various polyclonal sera and monoclonal antibodies against different regions of the HERV-K10 gag or env polyprotein, the instant invention identifies and describes the processed gag proteins and their use to detect HERV-K10-specific antibodies present in samples from the human body. Furthermore, the HERV-K10 gag or env proteins expressed in the baculovirus system are used to detect HERV-K10-specific antibodies present in human sera from patients with testicular tumors, particularly seminoma.

a) Construction and induction of recombinant procaryotic expression vector

Figure 1C:
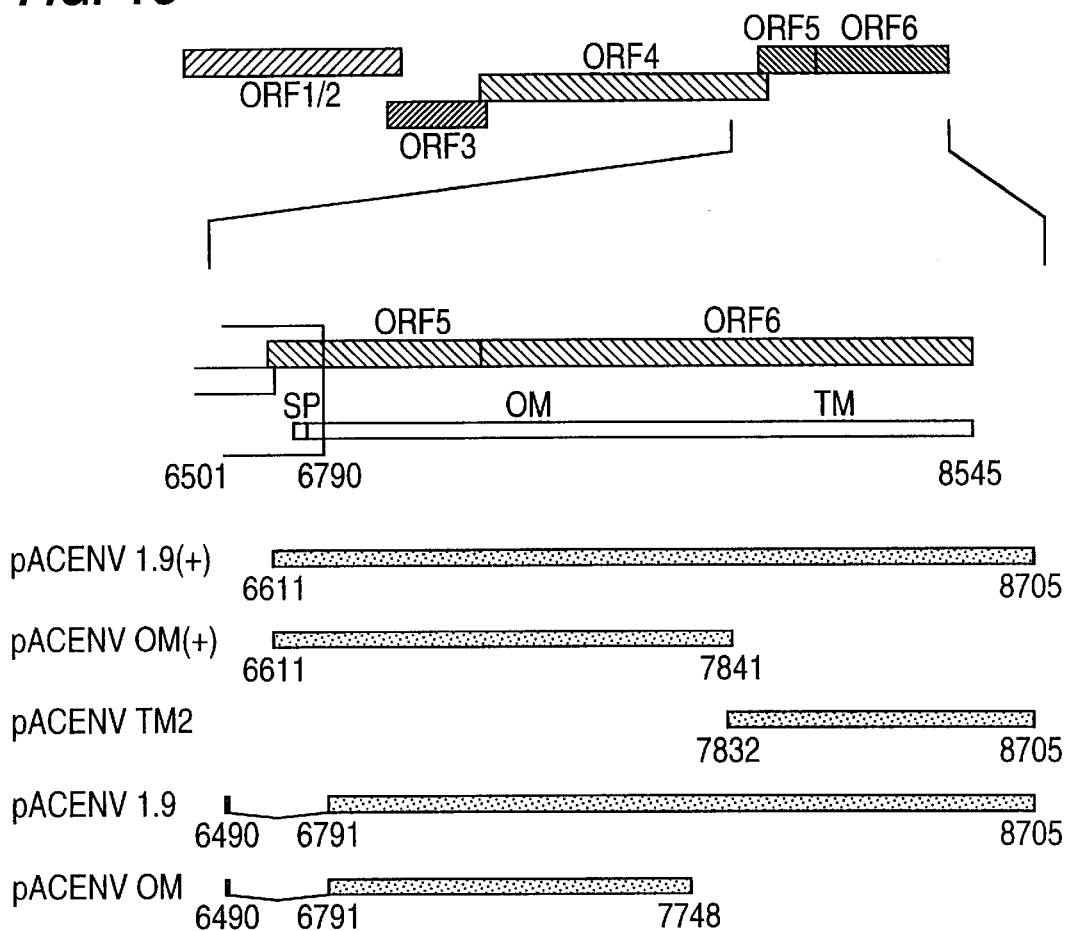
FIG. 1C is a schematic representation of the plasmids which are used for procaryotic expression of HERV-K10 env in pATH. Homologous inserts of the baculovirus constructs pACENV 1.9, pACENV1.9(+), pACENVOM, PACENVOM(+) and PACENVTM2 were cloned in the procaryotic vector system pATH: pKENV1.9, pKENV1.9(+), pKENVOM, pKENVOM(=), and pKENVTM2. The protein products encoded by these constructs are analyzed by immunoblotting technique. The plasmid pACENV1.9(+) contains a stop codon at nucleotide number 8431 of Ono et al., supra, which is not detectable in the construct pACENVTM2.

The location of all constructs on the HERV-K10 genome is shown in FIGS. 1A, 1B and 1C. The plasmids pKG-P, pKG and pAUR-1 have been described recently. Mueller-Lantzsch, et al., supra (1993). To generate pKP0.8, the EcoRI/MscI fragment excised from pKG-P is cloned into pATH11 (Koerner, et al., *Methods-Enzymol.* 194:477 (1991)) digested with EcoRI and SmaI. To generate pKN0.7 the EcoRI/EcoRV fragment excised from pKG is cloned into pATH11 digested with EcoRI and SmaI. The plasmids pKP0.8 and pKN0.7 encode fusion proteins containing 37 kDa of the amino terminus of the anthranilate synthetase (TrpE) of *E.coli* and the C-terminal (pKP0.8) or the N-terminal (pKN0.7) part of the HERV-K10 Gag protein.

*E.coli* BL21-DE-3 is transformed with the plasmids and induction of the fusion proteins carried out as described. The fusion proteins are used to produce polyclonal antisera.

b) Production of polyclonal rabbit antibodies

The fusion proteins of the instant invention are purified by electrophoresis in 10% SDS-polyacrylamide gels and used to immunize rabbits as described previously. Miller, et al, *Proc. Natl. Acad. Sci. USA* 70:190 (1973). The rabbit sera raised against the fusion proteins encoded by the plasmids pKG, pKN0.7 and pKP0.8 are referred to as serum No. 6897 (anti-gag serum), serum No. 266 (anti gag N-terminus serum) and serum No. 8037 (anti gag C-terminus serum). Rabbit antisera can also be raised against the proteins encoded by the plasmids pACENV1.9(+), pACENV1.9, pACENVTM2 and pACENVOM.

c) Characterization of the HERV-K10 gag proteins

In order to delineate the processed HERV-K10 Gag proteins from the 73 KDa Gag polyprotein, a DNA fragment containing the entire gag reading frame and the adjacent protease region construct pKG-P (FIG. 1B) is inserted into the expression vector pATH11 and expressed in *Escherichia coli* BL21-DE-3 according to the method described in Mueller-Lantzsch, et al., supra (1993), the entirety of which is hereby incorporated by reference.

Protein extracts are analyzed by protein immunoblot using monoclonal antibodies or polyclonal rabbit sera directed against different parts of the HERV-K10 Gag polyprotein as shown in FIG. 2A. Proteins are separated on SDS polyacrylamide gels (SDS-PAGE) and electrophoretically transferred to Immobilon membranes (Millipore Corp.). Towbin, et al., *Proc. Natl. Acad. Sci. USA* 76:4350 (1979). The blots are incubated with rabbit antisera at a dilution of 1:200 and then stained indirectly by using peroxidase-conjugated goat anti-rabbit antibodies. When the staining is performed by the Enhanced Chemiluminescent technique (ECL) (Amersham), nitrocellulose membrane is used for the electrophoretic transfer.

Using the polyclonal rabbit serum specific for HERV-K10 gag, three dominant protein bands with molecular weights of 30 KDa, 26 KDa and 22 KDa could be observed while a monoclonal antibody directed against the C-terminal part of HERV-K10 Gag reacted predominantly with two proteins of 15 and 16 KDa. A polyclonal rabbit serum directed against 228 amino acids of the N-terminal part exhibited the strongest reaction against the 22 KDa protein. Antisera or monoclonal antibodies specifically directed against the N- or C-terminal or against the central part of HERV-K10 Gag are generated. By using these antibodies to analyze its prokaryotic expression or expression in Tera 1 cells it is possible to determine the tentative sequence of the processed gag proteins. Both the pro- and eukaryotic expression revealed that at the C-terminal end of the Gag polyprotein approximately a 15 KDa protein is located followed by a 30 KDa protein. Analyzing the HERV-K10 expression in Tera 1 cells, a 18 KDa protein could clearly be determined to be located at the N-terminal end of HERV-K10 Gag, while the exact localization of three proteins with 22 KDa, 19 KDa and 17 KDa derived from the central part of Gag could not definitively be assigned. Similarly, in *E.coli* the exact order of the 26 KDa and 22 KDa proteins derived from the N-terminus are not determined.

d) Production of monoclonal antibodies

The plasmids pAUR-1 and pKP0.8 encoding the central and the N-terminal part of the HERV-K10 Gag protein, respectively (FIG. 1B), are used to produce monoclonal antibodies. The fusion proteins are isolated as described above. Approximately 20 μg of SDS-PAGE-purified fusion protein dissolved in 200 μl PBS and emulsified with 200 μl of Freund's complete adjuvant are injected intraperitoneally and subcutaneously into Lou/c rats (E20, Bazin JIM 112:53). On day 21, the procedure is repeated with Freund's incomplete adjuvant. Three days before fusion, a final boost without adjuvant is given intraperitoneally. Fusion of the myeloma P3X63Ag8.653 with the rat immune spleen cells is performed according to the general procedure described by Kohler, et al., *Nature* 256:495 (1975). Hybridoma supernatant are tested in a solid-phase immunoassay using bacterial extract from either *E.coli* expressing the parental non-fusion TrpE protein or HERV-K10 Gag fusion protein.

Polystyrene microtiter plates (Greiner, Germany) are coated with the crude *E.coli* extracts diluted 1:200 in carbonate-bicarbonate buffer (50 mM, pH 9.5), as determined with anti-TrpE monoclonal antibody (M1). The wells are blocked with PBS containing 1% non-fat milk (Fink, Germany). Culture supernatant are incubated for 1 hour and bound rat monoclonal antibodies are detected with goat anti-rat IgG coupled with horseradish peroxidase (Dianova, Germany), using O-phenylendiamine (OPD; Sigma, Germany) as substrate. Antibody-producing hybridomas which reacted positively with the HERV-K10 Gag fusion protein and negatively with non-fusion TrpE protein are tested against fusion protein of the C-terminal or middle part of the HERV-K10 Gag and cloned at least twice by limiting dilution. The immunoglobulin type is determined in a solid-phase ELISA with mouse anti-rat antibodies as capture and biotinylated monoclonal mouse anti-rat Ig class (anti-IgM, Zymed) and anti-IgG subclass antibodies as indicators. Springer, Hybridoma 1:257 (1982). The positive clones are confirmed by immunofluorescence using full-length Gag protein expressed in SF158 insect cells.

In the reaction of a monoclonal antibody directed against the central part of HERV-K10 Gag the 30 KDa is found to exhibit strong activity while a protein band of 26 KDa reacted to a smaller extend. Additional protein bands on the upper part of the gel with extremely strong reaction presumably represent the partially processed HERV-K10 Gag polyprotein. Several protein bands in the lower part of the gel might represent degradation products of HERV-K10 Gag due to the presence of bacterial proteases.

The data obtained from the monoclonal immunoblot experiments shown in FIG. 2A clearly locate the 15 and 16 KDa protein at the C-terminus. Next to these proteins, the 30 KDa protein is located, while good evidence exists for the location of the 22 KDa protein at the N-terminus. Finally the 26 KDa protein seems to be encoded by a central region between the 22 and the 30 KDa protein. A proposed model for the processing of the HERV-K10 Gag-protein is shown in FIG. 3A.

e) Eukaryotic expression of HERV-K10 gag and env

Figure 6:
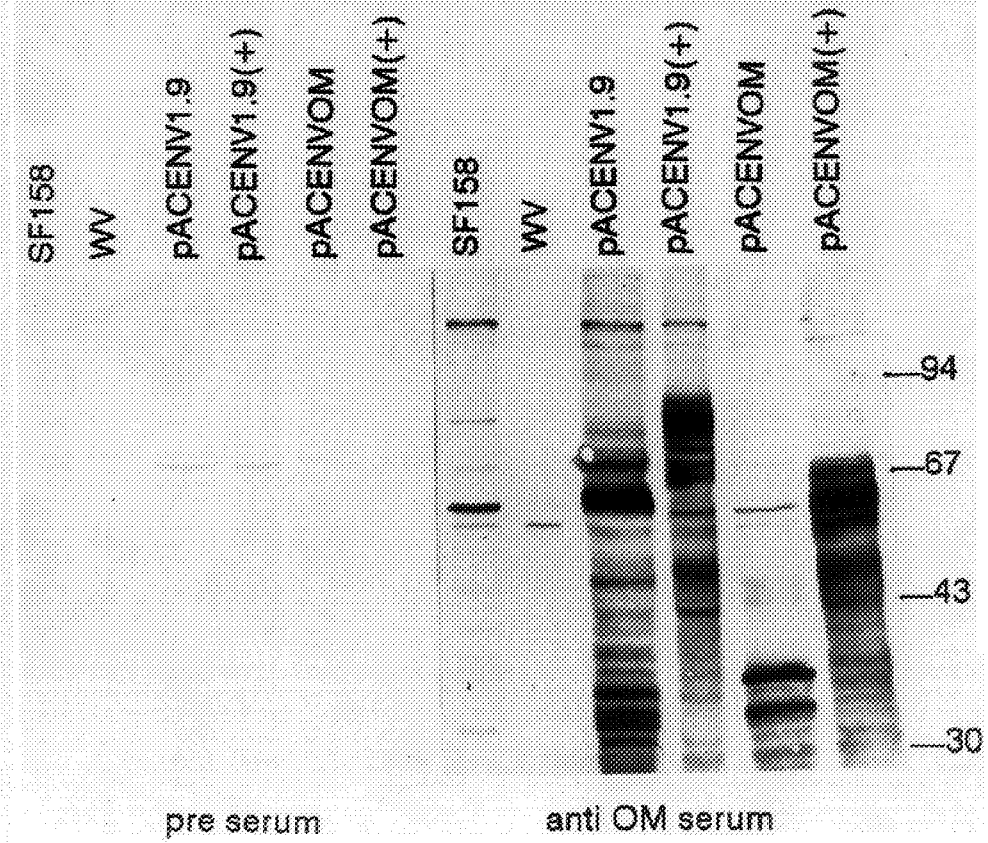
FIG. 6. Immunoblot analysis of the env homologous region expressed in the baculovirus system. The insect cells *Spodoptera frugiperda* (SF158) are infected either with the wild type baculovirus *Autographa californica* (WV) or with a recombinant baculovirus containing different parts of the env-homologous region, as described in FIG. 1C. The cells are harvested 24 hours after infection, suspended in sample buffer and 5 $\mu$g of the protein is subjected to a 12.5% SDS-PAGE following blotting analysis with the anti-OM serum or as control with the preimmune serum.

Various constructs containing the HERV-K10 env gene are expressed in the eukaryotic baculovirus system. The plasmids pACENV1.9 and pACENVOM, which both lack the SP and N terminus of the env gene, produce proteins with molecular weights in the range of about 64 kDa or 35 kDa, respectively, as shown in FIG. 6. In contrast, the plasmids pACENV1.9(+), pACENVOM(+), which both contain the SP according to the sequence of HERV-K10(+), produce proteins with much higher molecular weights than calculated from their encoded amino acid sequences. This difference may be due to the fact that env proteins of retroviruses are glycosylated.

N-linked glycosylation is inhibited by treating the recombinant baculovirus infected cells with tunicamycin. FIG. 7A. The molecular weights of the proteins expressed by cells containing the baculovirus constructs pACENV1.9 and pACENVOM, which both lack the sequences for SP, are not affected by tunicamycin treatment. In contrast, the proteins expressed from cells containing the baculovirus constructs pACENV1.9(+) or pACENVOM(+) have a remarkably reduced molecular weight. Since both pACENV1.9(+) and pACENVOM(+) possess the sequences for the SP, the SP is necessary for N-linked glycosylation of the env protein of HERV-K10.

f) Construction of baculovirus transfer vector and generation of recombinant baculoviruses 1. HERV-K10 gag-expression An AatII/HindIII fragment excised from the vector pUC19 is cloned into pKG digested with AatII and HindIII. The resulting plasmid pUCGAG is digested with KpnI. After isolation of a KpnI-resistant gag-specific fragment it is cloned in a KpnI-digested pUC19 vector. From this plasmid, designated pUC-GAG*, a SmaI/MscI fragment is isolated and cloned into a SmaI-digested baculovirus transfer vector pAC409. The resulting plasmid, called pACGAG, is used to generate the recombinant baculovirus. The insect cells SF158 are co-transfected with wild-type baculovirus *Autographa californica* nuclear polyhedrosis virus (AcNPV). Extracellular virions and viral genomic DNA are prepared by methods known to those of skill in the art. Summers, et al. *Texas Agric. Exp. Stat. Bull. no.* 1555 (1987). Genomic DNA and the recombinant transfer vector pACGAG are prepared as described by Frech, et al., *J. Virol.* 64:2759 (1990).

2. HERV-K10 env expression

Plasmids pACENV1.9(+), pACENV1.9, pACENVOM (+) and pACENVOM are expressed in the eukaryotic baculovirus system. SF158 is a continuous insect cell line derived from *Spodoptera frugiperda*. Summers, et al., *Texas Agric Exp Stat Bull no.* 1555 (1987). Cells are maintained as described previously. Frech, et al., supra (1990). Wild-type baculovirus *Autographa californica* nuclear polyhedrosis virus (AcNPV) is amplified by infection of SF158 cells. Extracellular virions and viral genomic DNA are prepared as described. Summers, et al., supra (1987). The *E.coli* strain BL21-DE-3 has been described. Smith, et al., supra (1987). Cell culture supernatants are prepared as discussed above.

EXAMPLE 3

Distribution of HERV-K10 Gag and Env Specific Antibodies in the Human Population In order to search for a potential pathophysiological role of HERV-K10, the gag and/or env region is expressed in the baculovirus system. The recombinant protein is utilized to screen human sera for antibody reactivity by employing the immunofluorescence technique.

Indirect immunofluorescence (IF) for the determination of antibody titers; against HERV-K10 gag or env is carried out as follows: SF158 cells in the logarithmic growth phase are infected with pACGAG for gag expression or pACENV1.9 (+), pACENV1.9 and pACENVTM2 for env expression. Similar constructs expressing HERV-K10 gag- or env-specific epitopes may also me used.

Wild-type baculovirus infected cells served as a control. Cells are harvested 42 hr post-infection and mixed with uninfected cells at a ratio of 1:40. Cover-slides are coated with the cell mixture and fixed at −20° C. for 10 min. in acetone. The cells are incubated for 45 min with human or rabbit sera diluted in PBS and stained by indirect immunofluorescence with fluorescein isothiocyanate-conjugated goat anti-human immunoglobulin G (IgG) or goat anti-rabbit IgG diluted 1:50, respectively.

For analyzing human sera, insect cells expressing HERV-K10 gag are diluted 1:40 with uninfected cells to reach a concentration of 5–15 gag positive cells per visual field in order to avoid an overpresentation of gag-antigen. Human sera are screened at an initial concentration of 1:40 and titrated in twofold dilutions. A variety of healthy individuals as well as patients with different diseases as indicated in Tables III-A and III-B are investigated.

The specific epitopes reacting in the immunof luorescence test are narrowed down to 54 amino acids at the N-terminal part of HERV-K10 gag. By computer analysis using the PALIGN program of PC/GENE (IntelliGenetics, Inc., Mountain View, Calif.) these amino acids showed a minor homology of 5 amino acids to the gag genes of Mason-Pfizer monkey virus, Jaagsiekte sheep retrovirus and squirrel monkey retrovirus but no homology to other known viruses or cellular genes. Therefore, we believe that the antibodies found among human individuals and patients are specifically induced by the expression of HERV-K10 Gag.

Immunofluorescence using pACENV OM and human sera were negative. The results using recombinant pACENV OM(+) were positive, but weaker than results using pACENV 1.9(+). Thus, the better recombinant products for detecting immunofluorescently reactive HERV-K10 env protein is either pACENV OM(+) or pACENV 1.9(+).

Low titers of antibodies against the N-terminal part of HERV-K10 gag and against an HERV-K10 env protein containing the transmembrane region can be detected in only approximately 0.1–0.5% of healthy individuals. While patients with particularly different tumor diseases exhibit antibodies against HERV-K10 env or HERV-K10 gag in about 1.1% or 1.5% of cases, respectively, only one case among 200 healthy individuals (controls) exhibited a titer against HERV-K10 env. The specificity of the instant HERV-K10 env protein for detecting seminoma contradicts the results of Vogetseder et al., *AIDS Res. Hum. Retroviruses* 9:687 (1993). Vogetseder et al. found antibodies against procaryotically expressed HERV-K10 env protein in about 12% of healthy controls as well as patients with different diseases. The reason for the specificity of the HERV-K10 env proteins of this invention for seminoma is likely based on the structural differences between the HERV-K10 env proteins of this application and those of Vogetseder et al. The HERV-K10 env proteins of Vogetseder et al. include only the outer membrane of the envelope. Because the pACENV1.9 expressed HERV-K10 env proteins of this application are able to detect antibodies while the pACENVOM expressed proteins of this application are not, Dr. Mueller-Lantzsch and Dr. Sauter recognize that most human antibodies directed against HERV-K10 env are directed against the TM-region. Therefore, a preferred HERV-K10 env protein of the instant invention contains the transmembrane region of HERV-K10 env, or immunoreactive portions thereof, for use in identifying/detecting the presence of seminoma in a patient, lowering the potential for false positive reactions and for treating seminoma-positive patients.

A summary of the determination of antibodies against HERV-K10 gag in sera from patients with non-tumor and tumor diseases is shown in Tables III-A and III-B, respectfully. Patients with seminoma have antibody titers to HERV-K10 gag or env in the range of 1:2560 at the time when the tumor was detected. One exception was found in a patient with a non-Hodgkin lymphoma with a titer of 1:2560. In contrast, 31% of patients with tumors composed of seminoma, teratoma, teratocarcinoma or mixed germ cell tumors exhibit antibodies against HERV-K10 gag and 53% of such patients exhibit antibodies against HERV-K10 env with titers up to 1:20480. Sixty five percent of patients with seminoma had antibody titers against HERV-K10 gag ranging between 1:40 and 1:20480. Eighty-five percent of patients with seminoma had antibodies against HERV-K10 env. An even higher percentage (78%) of patients with seminoma exhibited antibody titers at the time of diagnosis or when recidives occurred. This observation was confirmed by the analysis of three follow up sera from one patient which indeed only contained a high amount of antibodies at the time of tumor detection and before therapy. Only one of fourteen patients with seminoma in remission exhibits antibodies against env and none of the fourteen patients with a seminoma in remission exhibited antibodies against gag. See Table II.

a) Immunohistological Detection of Seminoma Metastases

The instant invention has determined that the HERV-K10 gag and env-specific antibodies present in seminoma patients were indeed due to the presence of HERV-K10 antigens in the tumor. The expression of HERV-K10 gag protein in biopsy material of patients with seminoma and related tumors is analyzed either by immunohistochemistry or immunoblotting. The use of both methods demonstrates that in seminoma tumor biopsies from seropositive patients as well as in seminoma patients where no antisera were available, protein with HERV-K10 gag or env reactivity could be reproducibly identified. Using either indirect immunofluorescence or immunohistochemistry, prior art methods and compositions, as disclosed in WO94/11514, were unable to detect a 67 kd glycosylated HERV-K10 env protein. The instant inventors were the first to demonstrate that HERV-K10 gag and env proteins are synthesized in seminoma tumor cells and that a high percentage of patients with those tumors exhibit elevated antibody titers against gag. Furthermore, the data obtained with the follow-up sera of one patient suggest that antibodies in seminoma tumor patients have diagnostic and prognostic value. The specific role that HERV-K10 plays in the development of seminoma is not clear. Of the 11 tumors of germ line origin tested for the expression of HERV-K10 gag, eight were shown to express these proteins specifically. Sauter et al., supra 1995.

b) Immunohistochemistry

Formalin-fixed paraffin-embedded testicular tumor tissue or, as a control, Tera 1 cells are sectioned at 4 $\mu$m, deparaffinized, rinsed in PBS and incubated 30 min in hydrogen peroxide (0.6% in methanol), and rinsed again in PBS. The tissue sections are pre-treated in citrate buffer (0.01 M; pH 6.0) in a microwave oven for 5 min at 600 W, 5 minutes at 450 W. After cooling to room temperature, the sections are incubated with swine serum for 20 minutes. For immunostaining the slides are incubated at room temperature with the rabbit anti HERV-K10 gag or env serum or, as a control, preimmune serum diluted 1:40 for 1–2 hours followed by incubations with biotin-conjugated swine anti-rabbit antibodies, diluted 1:200 (DAKO), for 30 min, and with avidin-biotin complex, diluted 1:100 (DAKO), for 30 min. and developed with diaminobenzidine (DAB). After each incubation step, the slides are rinsed in PBS for 5 minutes.

c) Immunoblotting analysis of tumor biopsies

Tissue samples stored at −70° C. are homogenized on ice in sample buffer. After incubating at 95° C. for 10 min and centrifugation for 10 min at 15,000×g the supernatant is analyzed by SDS-PAGE and immunoblotting as reported recently. Sauter, M. and N. Mueller-Lantzsch, *Virus Res.* 8:141 (1987).

d) Competition assays

In competition fluorescence assays, the antisera used for staining are preincubated with 2 $\mu$g of isolated fusion protein or anthranilate synthetase protein per ml over night at 4° C. In competition immunoblot assays the preincubation is carried out in 10% non-fat milk.

The specificity of the immunofluorescence reaction is proven by competition experiments using different recombinant fusion proteins of HERV-K10 Gag (pKG, pAUR-1, pKP0.8, pKN0.7) as shown in FIG. 1. The results in Table IV clearly indicate that the Gag fusion protein covering the N-terminal part or the entire gag region of HERV-K10 gag completely inhibited binding of the serum antibodies to the Gag protein while fusion proteins from the middle or c-terminal part as well as the bacterial part of the fusion protein (Trp E) achieved no or only minor effect. These data provide evidence that the major epitopes recognized by positive human sera are located probably within the 54 N-terminal amino acids of Gag while no reactivity against the central part of Gag was detectable.

e) Expression of HERV-K10 Gag protein in tumor biopsies

The presence of antibodies against HERV-K10 Gag predominantly in patients with seminoma rose the possibility that this protein might be expressed in the tumor itself. In order to prove this hypothesis tumor biopsies from patients with antibody titers against HERV-K10 Gag are tested by immunohistochemistry and immunoblotting analysis for the expression of HERV-K10 Gag.

Sections of formalin-fixed paraffin wax blocks from a seminoma mixed with embryonal carcinoma cells or a pure seminoma are stained by using a rabbit antiserum (serum No. 6897) directed against the entire HERV-K10 Gag as described above for the production of polyclonal antiserum. Immunohistochemistry analysis of (1) Tera 1 cells, (2) biopsies from patients with a seminoma and a combined embryo carcinoma or (3) with seminoma was performed using sections from formalin-fixed paraffin-embedded tumor tissue or Tera 1 cells. The sections are incubated with rabbit anti-HERV-K10 Gag serum No. 6897 followed by biotin-conjugated swine anti-rabbit serum and incubation with an avidin-biotin complex. The immunostaining is performed with DAB. The results indicate that Gag-related proteins could be detected in the form of clusters concentrated within the cytoplasm of the tumor cells. (Results not shown; See color photographs in FIG. 5 of Sauter, et al., *J. Virol.* 69:414 (1995). In contrast, in the surrounding tissue or in tissue of healthy testes no positive reaction could be found. The positive controls, which were acetone fixed insect cells expressing recombinant HERV-K10 gag or formalin-fixed and paraffin wax-embedded Tera 1 cells showed the positive reactive material predominantly concentrated in the cytoplasm.

Figure 5A:
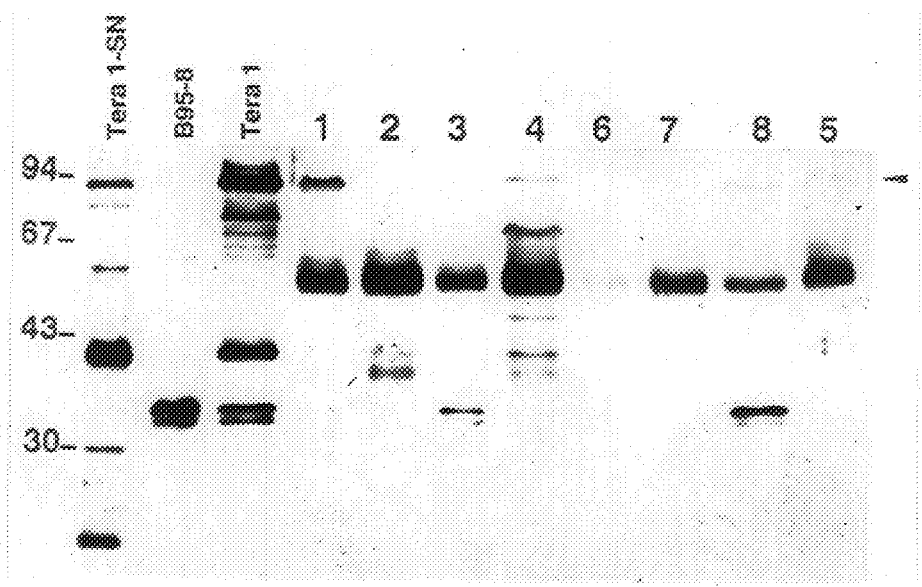
FIGURES 5A and 5B. Immunoblot analysis of testicular tumor biopsies (FIG. 5A, lanes 1–6 and FIG. 5B, lanes 1–6). Tissue samples are homogenized on ice in sample buffer. After incubating at 95° C. for 10 min. and centrifugation for 10 minutes at 15000×g, the supernatant is analyzed (lanes 1–8). From every material 15.5 82 g protein is subjected to a 12.5% SDS-PAGE. After blotting, the membranes are probed with rabbit serum No. 6897 directed against the entire Gag protein (pKG) (FIG. 5A), or with monoclonal antibodies directed against the middle part of the Gag protein (pAUR-1) (FIG. 5B). Tera 1 cells serves as positive and B95-8 cells as negative controls.
Figure 5B:
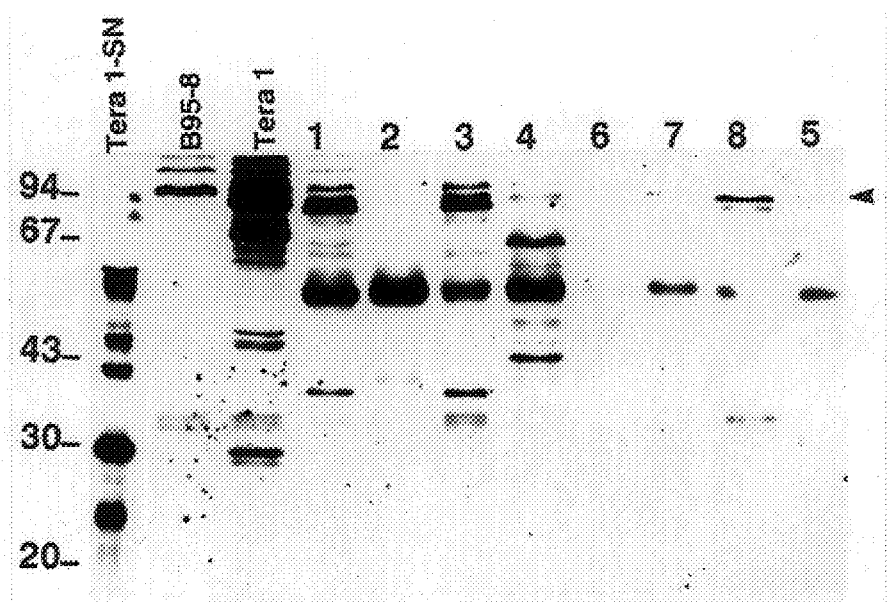

From a few biopsies, frozen material was available. These tissues are processed and analyzed by immunoblotting using rabbit anti HERV-K10 Gag serum (serum No. 6897) or monoclonal antibodies to Gag as described above. The rabbit anti-gag serum specifically recognizes a protein band of 80 KDa which presumably represents the Gag polyprotein which was predominantly found in biopsy 1, while in biopsy Nos. 3, 4, 8 and 5 only a weak reaction could be observed (FIG. 5A). Using a monoclonal antibody directed against the middle part of HERV-K10 Gag, the 80 KDa protein band was clearly detected in biopsy Numbers 1, 3, 4 and 8 (FIG. 5B).

Several background bands with a molecular weight of about 50 KDa are found by using both antisera or monoclonal antibodies. At the present time nothing is known about the nature of those 50 KDa proteins. In competition experiments using full length recombinant fusion protein of HERV-K10 Gag (pkG) for preincubation of the specific rabbit serum (No. 6897) or monoclonal antibodies the binding of specific antibodies to the 80 KDa protein from biopsies No. 1 and 8 could be abolished.

It should be mentioned that in the *E.coli* expression system the monoclonal antibody directed against the middle part of HERV-K10 Gag as well as the monoclonal antibody against the C-terminal part recognized the processed Gag proteins only but reproducibly did not react with the 80 KDa Gag polyprotein. One possible explanation for this different reaction pattern could be that the relevant epitopes are not accessible for the described monoclonal antibodies on the Gag-TrpE fusion protein due to an overload by other bacterial proteins.

EXAMPLE 4

ELISA for Detecting HERV-K10 Gag and/or Env

To test blood samples for antibodies that bind specifically to the recombinant HERV-K10 antigens, the following procedure was employed. After the recombinant HERV-K10 env or gag proteins are purified, such as the purification of glutathione-HERV-K10 env or gag fusion proteins on glutathione agarose, the recombinant protein is diluted in PBS to a concentration of 5 ug/ml (500 ng/100 $\mu$l ). One hundred microliters of the diluted antigen solution was added to each well of a 96-well Immulon 1 plate (Dynatech Laboratories, Chantilly, Va.), and the plate was then incubated for 1 hour at room temperature, or overnight at 4° C., and washed 3 times with 0.05% Tween 20 in PBS. Blocking to reduce nonspecific binding of antibodies is accomplished by adding to each well 200 μl of a 1% solution of bovine serum albumin in PBS/Tween 20 and incubation for 1 hour. After aspiration of the blocking solution, 100 μl of the primary antibody solution (anticoagulated whole blood, plasma, or serum), diluted in the range of 1/16 to 1/2048 in blocking solution, is added and incubated for 1 hour at room temperature or overnight at 4° C. The wells are then washed 3 times, and 100 μl of goat anti-human IgG antibody conjugated to horseradish peroxidase (organon Teknika, Durham, N.C.), diluted 1/500 or 1/1000 in PBS/Tween 20, 100 μl of o-phenylenediamine dihydrochloride (OPD, Sigma) solution is added to each well and incubated for 5–15 minutes. The OPD solution is prepared by dissolving a 5 mg OPD tablet in 50 ml 1% methanol in $H_2O$ and adding 50 μl 30% $H_2O_2$ immediately before use. The reaction is stopped by adding 25 l of 4M $H_2SO_4$. Absorbance are read at 490 nm in a microplate reader (Bio-Rad).

EXAMPLE 5

Diagnostic Imaging Using HERV-K10 Gag and Env Specific Antibodies

Accurately staging seminoma patients at initial presentation and early detection of metastatic spread of seminoma can utilize the instant disclosure of the presence of HERV-K10 gag and env proteins in seminoma cells. Radioimmunoscintigraphy using monoclonal antibodies specific for HERV-K10 gag or HERV-K10 env can provide an additional tumor-specific diagnostic test. The monoclonal antibodies of the instant invention may be used for histopathological diagnosis of testicular and extra-testicular seminomas.

Subcutaneous human xenografts of seminoma cells in nude mice can be used to test whether a technetium-99m ($^{99m}$Tc)-labelled monoclonal antibody of the invention can successfully image the xenografted seminoma by external gamma scintigraphy. Marks, et al., supra (1990). Each monoclonal antibody specific for either HERV-K10 gag or env is purified from ascitic fluid of BALB/c mice bearing hybridoma tumors by affinity chromatography on protein A-Sepharose. Purified antibodies, including control monoclonal antibodies such as the avidin-specific monoclonal antibody of Dr. Mark McDermott (Skea, et al., *J. Immunol.* 151:3557 (1993).) are labelled with $^{99m}$Tc following reduction, using the methods of Mather, et al., *J. Nucl. Med.* 31:692 (1990) and Zhang et al., *Nucl. Med. Biol.* 19:607 (1992). Nude mice bearing human seminoma cells or the HEY cell line (Marks, et al., supra) are injected intraperitoneally with 200–500 μCi of $^{99m}$Tc-labelled antibody. Twenty-four hours after injection, images of the mice are obtained using a Siemens ZLC3700 gamma camera equipped with a 6 mm pinhole collimator set approximately 8 cm. from the animal. To determine monoclonal antibody biodistribution following imaging, the normal organs and tumors are removed, weighted, and the radioactivity of the tissues and a sample of the injectate are measured. HERV-K10-specific antibodies conjugated to antitumor compounds may also be used as seminoma-specific chemotherapy.

EXAMPLE 6

Vaccines That Immunize Against HERV-K10 Expressing Tissues

The present invention also relates to a method of stimulating an immune response against seminoma cells, or cells that express HERV-K10 gag or env polypeptides in a patient using HERV-K10 gag and/or env polypeptides of the invention that acts as an antigen produced by or associated with a malignant cell. This aspect of the invention provides a method of stimulating an immune response in a human against seminoma cells or cells that express HERV-K10 env or gag polypeptides, which comprises the step of administering to a human an immunogenic amount of an a polypeptide comprising: (a) the amino acid sequence of a human endogenous retrovirus K10 protein or (b) a mutein or variant of a polypeptide comprising the amino acid sequence of a human endogenous retrovirus K10 protein.

It will be apparent to those skilled in the art that various modifications and variations can be made to the compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

TABLE IA

Summary of Sequence Analyses of HERV-K10 Clone pKG-P

| Position in the published sequence of HERV-K10 | Nucleotide exchanges found in the clone pKG-P | | Amino acid exchanges found in the clone pKG-P | |
|---|---|---|---|---|
| | From | To | From | To |
| 1192 | A | G | | |
| 1275 | C | T | Ser | Leu |
| 1503 | A | C | His | Pro |
| 1622 | A | G | Met | Val |
| 1680 | T | C | Leu | Pro |
| 1731 | A | C | Gln | Pro |
| 1749 | | +G | Frame shift to ORF2 | |
| 1754 | T | C | Leu | Pro |
| 1755 | G | A | Leu | Pro |
| 1835 | C | A | Pro | Gln |
| 1871 | T | C | Met | Thr |
| 1912 | A | G | Ile | Val |
| 2388 | T | C | — | |
| 2463 | C | T | — | |
| 2499 | A | G | — | |
| 2524 | G | C | Gly | Arg |

TABLE IA-continued

Summary of Sequence Analyses of HERV-K10 Clone pKG-P

| Position in the published sequence of HERV-K10 | Nucleotide exchanges found in the clone pKG-P | | Amino acid exchanges found in the clone pKG-P | |
|---|---|---|---|---|
| | From | To | From | To |
| 2751 | T | C | — | |
| 2782 | A | G | Aes | Asp |
| 2886 | T | A | — | |
| 2937 | C | T | Overlapping ORF1/2 | |
| 2936 | A | G | Overlapping ORF3 | |
| 3125 | A | C | — | |
| 3170 | T | C | — | |
| 3188 | A | C | — | |
| 3195 | G | A | Glu | Lys |
| 3296 | A | G | — | |
| 3330 | A | T | Ser | Cys |
| 3336 | A | G | Arg | Gly |
| 3393 | A | C | Ile | Leu |
| 3400 | G | A | Arg | Lys |
| 3415 | T | G | Val | Gly |
| 3482 | T | C | — | |
| 3545 | T | C | — | |
| 3572 | C | T | — | |
| 3641 | G | T | Met | De |
| 3572 | G | A | — | |
| 3811 | T | G | Met | Arg |
| 3828 | | A | Leads to abort of ORF3 | |
| 3861 | G | A | — | |
| 3867 | G | T | — | |
| 3924 | T | C | Val | Ala |
| 3953 | C | T | — | |
| 4018 | G | A | — | |

TABLE IB

Sequence Analyses of different HERV-K10 Env Clones (1943 bp)

| | Nucleotide exchanges | Aminoacid exchanges | Size of proteins |
|---|---|---|---|
| pKENV 1.9 (+) | 22 | 14 | full-length |
| pKENV 1.9 (+) M | 23 | 14 | medium |
| pKENV 1.9 (+) K | 42 | 21 | small |

TABLE IC

Nucleotide exchanges by clone pKENV 1.9 (+)

| Position in the published sequence of HERV-K10 (+) | Nucleotide exchanges found in the clone pKENV 1.9 (+) | | Aminoacid exchanges found in the clone pKENV 1.9 (+) | |
|---|---|---|---|---|
| (Ono et al.. 1986) | from | to | from | to |
| after nt 6686 | +C | | frameshift from ORF 4 to ORF 5 | |
| 6838 | A | G | Ile | Val |
| ∩6940 | C | T | — | |
| 6947 | G | C | Arg | Thr |
| 6981 | T | C | — | |
| 7001 | C | T | Thr | Ile |
| 7156 | A | G | Asn | Asp |
| 7210 | T | C | Stop | Gln | combines ORF 5 and ORF 6 |
| 7534 | T | C | Cys | Arg |
| 7792 | G | A | Val | Ile |
| 7898 | C | G | Ala | Gly |
| 7965 | G | A | — | |
| 8120 | T | C | Phe | Ser |
| 8242 | G | A | Glu | Lys |
| 8355 | A | T | — | |
| 8356 | T | A | Ser | Thr |

TABLE IC-continued

Nucleotide exchanges by clone pKENV 1.9 (+)

| Position in the published sequence of HERV-K10 (+) (Ono et al.. 1986) | Nucleotide exchanges found in the clone pKENV 1.9 (+) from | Nucleotide exchanges found in the clone pKENV 1.9 (+) to | Aminoacid exchanges found in the clone pKENV 1.9 (+) from | Aminoacid exchanges found in the clone pKENV 1.9 (+) to | |
|---|---|---|---|---|---|
| 8358 | G | A | | | |
| 8431 | C | T | Arg | Stop | terminates ORF 6 |
| 8443 | G | A | Asp | Asn | |
| 8455 | C | T | Arg | Trp | |
| 8484 | G | A | — | | |
| 8526 | A | G | — | | |

TABLE II

EUCARYOTIC EXPRESSION OF THE ENV PROTEIN OF THE HUMAN ENDOGENOUS RETROVIRUS-K10 (HERV-k10) ND THE DETECTION OF ANTIBODIES AGAINST GAG- AND ENV-PROTEINS IN PATIENTS WITH TESTICULAR TUMORS

| Diagnosis | No. of Gag positive serum samples/no. of serum samples tested | % | No. of Env positive serum samples/no. of serum samples tested | % |
|---|---|---|---|---|
| Different diseases (Tumor diseases, HIV-positive etc) | 20/1173 | 1.5% | 15/1173 | 1.1% |
| Healthy individuals | 0/200 | 0% | 1/200 | 0.7% |
| Testicular tumors (primary-relapse-or in remission) | 45/115 | 39% | 70/115 | 61% |
| Seminoma (primary tumors or relapse) | 30/46 | 65% | 39/46 | 85% |
| Seminoma in remission | 0/14 | 0% | 1/14 | 7% |
| Other testicular abnormalities | 0/15 | 0% | 0/15 | 0% |

Testsystem: Indirect immunofluorescence of insect cells expressing HERV-K10 Ga or Env proteins (baculovirus system)

TABLE IIIA

DETERMINATION OF ANTIBODIES AGAINST HERV-K10 GAG IN SERA FROM HEALTHY INDIVIDUALS OR PATIENTS WITH NON-TUMOR DISEASES

| Diagnosis | Sera tested | Positive sera | Titer | % |
|---|---|---|---|---|
| Autoimmune diseases (Lupus erythematosus, MS, MCTD, Sklerodermia, Sharp, Sjögren, Cogan Syndrome, Arthritis) Immun. suppr. | 153 | 2 | 1:40 1:40 | 1.3% |
| | 53 | — | | 0% |
| HIV-positive | 113 | 3 | 1:160 1:160 1:80 | 2.7% |
| HIV-negative | 106 | 1 | 1:320 | 0.9% |
| Controls (students and hospital staff) | 233 | 1 | 1:40 | 0.4% |
| Total | 658 | 7 | | 1.0% |

TABLE IIIB

Determinations of Antibodies Against HERV-K10 Gag in sera from patients with tumor diseases

| Diagnosis | Sera tested | Positive sera | Titer | | % |
|---|---|---|---|---|---|
| Mamma Ca | 103 | 3 | 1:80 1:80 1:160 | | 2.9 |
| Brain tumor | 128 | 4 | 1:40 1:80 1:320 1:320 | 3.6 | |
| AML | 59 | | | | |
| Leukemia | 7 | — | 1:80 | | |
| ALL | 81 | 3 | 1:40 | | 3.7 |
| CML | 8 | — | 1:80 | | |
| CLL | 14 | — | | | |
| Non-Hodgkin Lymphoma | 63 | 3 | 1:2560 1:320 1:640 | | 4.8 |
| Hodgkin's disease | 164 | 3 | 1:80 1:40 1:80 | | 1.8 |
| Burkitt's-Lymphoma | 8 | — | | | 0 |
| Nasopharyngeal-Ca | 6 | — | | | 0 |
| "Hairy" Cell Leukoplakia | 1 | — | | | 0 |
| Colon Ca | 3 | — | | | 0 |
| Lymphoma | 88 | 2 | 1:40 | 1:640 | 2.3 |
| "Tumor disease" | 341 | 10 | 1:320 1:160 1:40 1:320 1:160 | 1:320 1:80 1:160 1:40 1:40 | 2.9 |
| Testicular tumors* | 17 | — | | | |
| Teratoma | 9 | 1 | 1:160 | | 11 |
| Seminoma | 31 | 14 | See Table II | | 45 |
| Total | 1131 | 43 | | | 3.9 |

*Testicular tumors: Mixed tumors: Leyding cell tumors: Embryonal CA: Urothelial CA

TABLE IV

Inhibition of HERV-K10 immunofluorescence[a]

| | Inhibition by: | | | | | |
|---|---|---|---|---|---|---|
| Serum | pATH 11 (vector) | pKG (total) | pAUR-1 (middle) | pKP0.8(C terminus) | pKN0.7(N terminus) | IF without competition |
| 1. Human | +(+) | 0 | + | + | 0 | + |
| 2. Human | ++ | 0 | (+) | + | 0 | ++ |
| 3. Human | + | 0 | (+) | (+) | 0 | ++ |
| 4. Human | ++ | 0 | ++ | ++ | 0 | ++ |
| 5. Human | +(+) | 0 | + | + | 0 | + |
| 6. Human | + | 0 | (+) | (+) | 0 | + |
| 7. Human | + | 0 | + | + | 0 | + |
| 8. Human | + | 0 | (+) | (+) | 0 | + |
| Rabbit anti-HERV-K10 Gag | ++ | 0 | ++ | ++ | +++ | +++ |

[a]Prior to immunofluorescence (1F) sera were preincubated with isolated fusion proteins encoded by constructs as indicated and described in Materials and Methods.
(+) a weak positive reaction.

What we claim is:

1. A method for detecting the presence of a seminoma in an individual by detecting the presence of an antibody to human endogenous retrovirus K10 (HERV-K10) in an individual, comprising the steps of:
   (A) contacting a sample from an individual potentially containing an anti-HERV-K10 antibody with a polypeptide comprising:
      (1) an amino acid sequence of a human endogenous retrovirus K10 gag protein, or
      (2) a mutein or variant of a polypeptide comprising the amino acid sequence of a human endogenous retrovirus K10 gag protein which is capable of detecting the presence of an antibody to human endogenous retrovirus K10;
   (B) allowing an anti-HERV-K10 gag antibody in said sample to bind to said polypeptide; and
   (C) determining whether an anti-HERV-K10 gag antibody present in said sample binds to said polypeptide.

2. A method for detecting the presence of a seminoma in an individual by detecting the presence of an antibody to human endogenous retrovirus K10 (HERV-K10), comprising the steps of:
   (A) contacting a sample from an individual potentially containing an anti-HERV-K10 env antibody with a polypeptide comprising:
      (1) an amino acid sequence of a human endogenous retrovirus K10 env protein, or
      (2) a mutein or variant of a polypeptide comprising the amino acid sequence of a human endogenous retrovirus K10 env protein which is capable of detecting the presence of an antibody to human endogenous retrovirus K10;
   (B) allowing an anti-HERV-K10 env antibody in said sample to bind to said polypeptide; and
   (C) determining whether an anti-HERV-K10 env antibody present in said sample binds to said polypeptide.

3. The method as claimed in claim 1, wherein said step (C) determines the presence of an anti-HERV-K10 gag antibody bound to said polypeptide by detecting the presence of said anti-HERV-K10 antibody using a compound selected from the group consisting of a colorometric agent, a fluorescent agent, a chemilluminescent agent and a radionuclide.

4. A kit for diagnosing the presence of a seminoma in an individual by detecting the presence of anti-HERV-K10 gag antibodies in a sample, said kit comprising a polypeptide comprising:
   (a) an amino acid sequence of a human endogenous retrovirus K10 gag protein, or
   (b) a mutein or variant of a polypeptide comprising the amino acid sequence of a human endogenous retrovirus K10 gag protein which is capable of detecting the presence of an antibody to human endogenous retrovirus K10.

5. A kit for diagnosing the presence of a seminoma in an individual by detecting the presence of anti-HERV-K10 env antibodies in a sample, said kit comprising a polypeptide comprising:
   (a) an amino acid sequence of a human endogenous retrovirus K10 env protein, or
   (b) a mutein or variant of a polypeptide comprising the amino acid sequence of a human endogenous retrovirus K10 env protein which is capable of detecting the presence of an antibody to human endogenous retrovirus K10.

6. A kit for diagnosing the presence of a seminoma in an individual by detecting the presence of anti-HERV-K10 antibodies in a sample, said kit comprising a polypeptide comprising:
   (a) an amino acid sequence of a human endogenous retrovirus K10 gag protein, or
   (b) a mutein or variant of a polypeptide comprising the amino acid sequence of a human endogenous retrovirus K10 gag protein which is capable of detecting the presence of an antibody to human endogenous retrovirus K10 and a polypeptide comprising an amino acid sequence of a human endogenous retrovirus K10 env protein.

7. The method of claim 1, wherein said polypeptide comprises an amino acid sequence of a human endogenous retrovirus K10 gag protein.

8. The method of claim 2, wherein said polypeptide comprises the amino acid sequence of a human endogenous retrovirus K10 env protein.

9. The kit of claim 4, wherein said polypeptide comprises an amino acid sequence of a human endogenous retrovirus K10 gag protein.

10. A kit for detecting the presence of a seminoma in an individual by detecting the presence of an antibody to human endogenous retrovirus K10 (HERV-K10), comprising a polypeptide comprising:
   (a) an amino acid sequence of a human endogenous retrovirus K10 env protein, or (b) a mutein or variant of a polypeptide comprising the amino acid sequence of a human endogenous retrovirus K10 env protein which is capable of detecting the presence of an antibody to human endogenous retrovirus K10.

11. A kit for detecting the presence of a seminoma in an individual, comprising a polypeptide comprising the amino acid sequence of a human endogenous retrovirus K10 env protein.

12. A kit for diagnosing the presence of a seminoma in an individual by detecting the presence of anti-HERV-K10 antibodies in a sample, said kit comprising a polypeptide comprising an amino acid sequence of a human endogenous retrovirus K10 gag protein and an amino acid sequence of a human endogenous retrovirus K10 env protein.

13. A kit for diagnosing the presence of a seminoma in an individual by detecting the presence of anti-HERV-K10 antibodies in a sample, said kit comprising a polypeptide comprising an amino acid sequence of a human endogenous retrovirus K10 gag protein.

14. A method for detecting the presence of seminoma, teratoma, teratocarcinoma or a mixed germ cell tumor in an individual by detecting the presence of an antibody to human endogenous retrovirus K10 (HERV-K10), comprising the steps of:

(A) contacting a sample from an individual potentially containing an anti-HERV-K10 env antibody with a polypeptide comprising:
   (1) an amino acid sequence of a human endogenous retrovirus K10 env protein, or
   (2) a mutein or variant of a polypeptide comprising the amino acid sequence of a human endogenous retrovirus K10 env protein which is capable of detecting the presence of an antibody to human endogenous retrovirus K10;

(B) allowing an anti-HERV-K10 env antibody in said sample to bind to said polypeptide; and (C) determining whether an anti-HERV-K10 env antibody present in said sample binds to said polypeptide.

15. A method for detecting the presence of a seminoma, teratoma, teratocarcinoma or a mixed germ cell tumor in an individual by detecting the presence of an antibody to human endogenous retrovirus K10 (HERV-K10), comprising the steps of:

(A) contacting a sample from an individual potentially containing an anti-HERV-K10 gag antibody with a polypeptide comprising:
   (1) an amino acid sequence of a human endogenous retrovirus K10 gag protein, or
   (2) a mutein or variant of a polypeptide comprising the amino acid sequence of a human endogenous retrovirus K10 gag protein which is capable of detecting the presence of an antibody to human endogenous retrovirus K10;

(B) allowing an anti-HERV-K10 gag antibody in said sample to bind said polypeptide; and (C) determining whether an anti-HERV-K10 gag antibody present in said sample binds to said polypeptide.

16. The method of claim 8, wherein said polypeptide comprises the transmembrane region of HERV-K10 env, or immunoreactive portions thereof.

17. The kit of claim 5, wherein said polypeptide comprises the transmembrane region of HERV-K10 env, or immunoreactive portions thereof.

* * * * *